United States Patent [19]

Okada et al.

[11] Patent Number: 5,548,054
[45] Date of Patent: Aug. 20, 1996

[54] FLUORINE-MODIFIED SILICONE DERIVATIVE, PRODUCTION THEREOF AND COSMETIC CONTAINING THE SAME

[75] Inventors: Jouji Okada, Ichikai-machi; Akira Kawamata, Utsunomiya; Tadayuki Tokunaga, Chiba; Noboru Nagatani, Funabashi; Makoto Torizuka, Kawasaki; Masahiko Asahi, Tokyo, all of Japan

[73] Assignee: Kao Corporation, Tokyo, Japan

[21] Appl. No.: 290,868

[22] PCT Filed: Feb. 23, 1993

[86] PCT No.: PCT/JP93/00223

§ 371 Date: Aug. 29, 1994

§ 102(e) Date: Aug. 29, 1994

[87] PCT Pub. No.: WO93/18085

PCT Pub. Date: Sep. 16, 1993

[30] Foreign Application Priority Data

Mar. 10, 1992 [JP] Japan .................................. 4-051640
Dec. 15, 1992 [JP] Japan .................................. 4-334143

[51] Int. Cl.$^6$ ..................... C08G 77/385; C08G 77/24
[52] U.S. Cl. ................... 528/25; 528/31; 528/42; 556/448
[58] Field of Search ................. 528/42, 31, 25; 556/448

[56] References Cited

U.S. PATENT DOCUMENTS

| 3,132,117 | 5/1964 | Schmidt | 528/42 |
| 4,549,004 | 10/1985 | von Au et al. | 528/42 |
| 4,985,526 | 1/1991 | Kishita et al. | 528/15 |
| 4,996,344 | 2/1991 | Inomata et al. | 556/448 |
| 5,124,467 | 6/1992 | Rodgers et al. | 556/427 |

OTHER PUBLICATIONS

Abstract JP 405247214 Sep. 1993.

*Primary Examiner*—Margaret W. Glass
*Attorney, Agent, or Firm*—Oblon, Spivak, McClelland, Maier & Neustadt, P.C.

[57] ABSTRACT

A fluorine-modified silicone derivative having an organopolysiloxane chain which is partly substituted by the siloxane chain of the following general formula (1), (2) or (3),

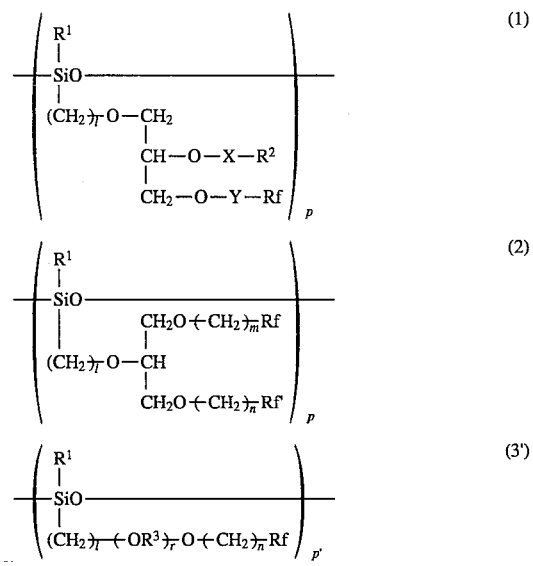

where $R^1$, $R^2$, $R^3$, $R_f$, $R_f'$, l, m, n and r are as described herein, a preparation process thereof, intermediates useful for the preparation thereof and cosmetic compositions containing this derivative.

3 Claims, No Drawings

FLUORINE-MODIFIED SILICONE DERIVATIVE, PRODUCTION THEREOF AND COSMETIC CONTAINING THE SAME

TECHNICAL FIELD

The present invention relates to a fluorine-modified silicone derivative, a preparation process thereof, and cosmetic compositions containing such a silicone derivative, and more particularly to a novel fluorine-modified silicone derivative having excellent water and oil repellency, a preparation process thereof, and cosmetic compositions containing such a silicone derivative and having good lastingness of makeup and feeling upon use.

BACKGROUND ART

Various water-repellent cosmetic compositions have heretofore been used with a view toward protecting the skin from water and sweat and preventing makeup from getting out of shape by water or sweat. For example, skin care cosmetic compositions such as skin creams and skin lotions, and makeup cosmetic compositions comprise a silicone oil or silicone resin as a water-repellent component. However, these silicone oil and resin can exhibit some effect on water repellency, but has no satisfactory effect on oil repellency. Therefore, cosmetic compositions in which these components are incorporated have a problem that they can not last makeup longer due to the excretion of sebum.

Therefore, attempts to develop a compound having both water repellency and oil repellency have been made in various fields. For example, Japanese Patent Application Laid-Open No. 295912/1990 discloses that a cosmetic composition in which a specific fluorine-modified silicone compound is incorporated is excellent in water resistance and sebum resistance.

Water- and oil-repellent base substances used in cosmetic compositions are required to satisfy all such conditions that (a) they have sufficient water and oil repellency for sweat and sebum, (b) they are excellent in emulsion stability and (c) they are not sticky to the touch and good in feeling upon use.

However, the above-described fluorine-modified silicone compound does not fully satisfy these requirements, in particular, oil repellency.

Accordingly, there has been a demand for development of a compound which is excellent in water and oil repellency, and moreover can last makeup longer when incorporated in a cosmetic composition and gives a user of the cosmetic composition a good feeling upon use.

In view of the foregoing circumstances, the present inventors have carried out an extensive investigation. As a result, it has been found that a specific fluorine-modified silicone derivative, which will be described subsequently, has excellent water and oil repellency and exhibits good compatibility with cosmetic components, thus leading to completion of the present invention.

DISCLOSURE OF THE INVENTION

The present invention is directed to a cosmetic composition comprising a fluorine-modified silicone derivative (A) having polysiloxane units selected from structural units represented by the following general formulae (1), (2) and (3) and polysiloxane units represented by the following general formula (4):

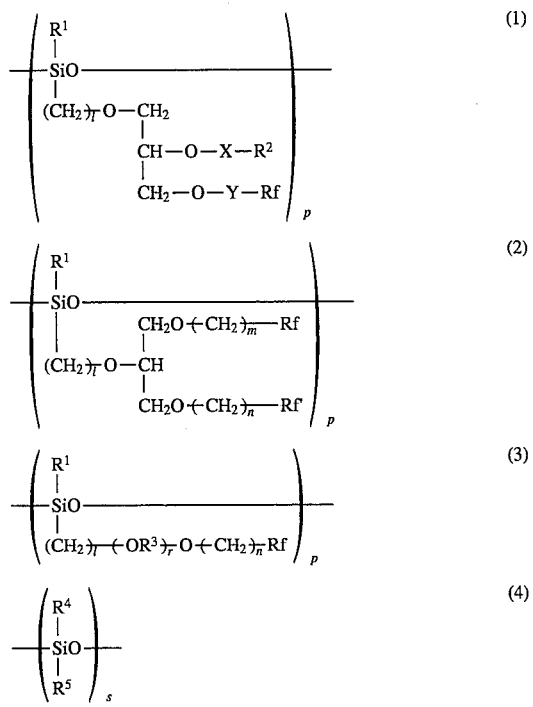

wherein Rf and Rf' mean individually a perfluoroalkyl group having 1–20 carbon atoms or a ω-H-perfluoroalkyl group represented by the formula $H(CF_2)_t$— in which t stands for an integer of 1–20, $R^1$, $R^4$ and $R^5$ may be identical with or different from each other and mean individually a straight-chain or branched aliphatic hydrocarbon group having 1–20 carbon atoms, or an alicyclic or aromatic hydrocarbon group having 5–10 carbon atoms, $R^2$ denotes a hydrogen atom, a straight-chain or branched aliphatic hydrocarbon group having 1–20 carbon atoms, an alicyclic or aromatic hydrocarbon group having 5–10 carbon atoms, a perfluoroalkyl group having 1–20 carbon atoms, or a ω-H-perfluoroalkyl group represented by the formula $H(CF_2)_u$— in which u stands for an integer of 1–20, $R^3$ is a divalent hydrocarbon group having 2–16 carbon atoms, X and Y mean individually a single bond, —CO— or a divalent hydrocarbon group having 1–6 carbon atoms, l stands for a number of 2–16, m and n are individually a number of 1–6, p is a number of 1–200, r is a number of 0–50, and s is a number of 0–200.

In the above-described fluorine-modified silicone derivatives (A), a fluorine-modified silicone derivative (B) having polysiloxane units selected from structural units represented by the following general formulae (1), (2) and (3') and polysiloxane units represented by the following general formula (4) is a novel compound not described in any literature, and the present invention is also directed to such a compound.

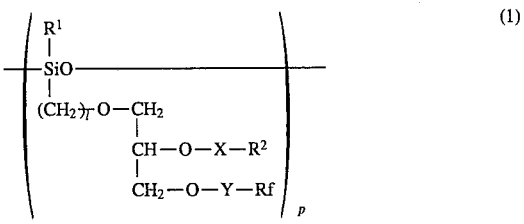

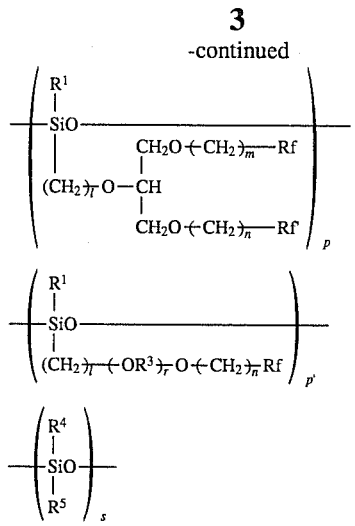

(2)

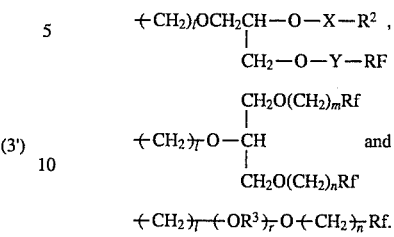

(3')

$$\left(\begin{array}{c} R^4 \\ | \\ -SiO- \\ | \\ R^5 \end{array}\right)_s$$

(4)

wherein p' stands for a number of 1-200, p'+S≧5, and Rf, Rf', $R^1$, $R^2$, $R^3$, $R^4$, $R^5$, l, m, n, p, s, X and Y have the same meaning as defined above.

Further, the present invention provides a preparation process of such a novel compound, and intermediates useful for the preparation of the novel compound.

According to the present invention, a fluorine-modified silicone derivative high in water repellency and oil repellency can be provided easily and simply. Besides, cosmetic compositions containing such a compound can last makeup longer and give users an excellent feeling upon use.

BEST MODE FOR CARRYING OUT THE INVENTION

In fluorine-modified silicone derivatives (A) and (B) according to the present invention, the hydrocarbon groups indicated by $R^1$, $R^2$, $R^4$ and $R^5$ include, for example, straight-chain alkyl groups such as methyl, ethyl, propyl, butyl, pentyl, hexyl, heptyl, octyl, nonyl and decyl; branched alkyl groups such as isopropyl, sec-butyl, tert-butyl, neopentyl, 1-ethylpropyl and 2-ethylhexyl; alicyclic groups such as cyclopentyl and cyclohexyl; and aromatic hydrocarbon groups such as phenyl and naphthyl.

Besides, as the (per) fluoroalkyl groups indicated by Rf, Rf' and $R^2$, either straight-chain groups or branched groups may be used. However, straight-chain groups are preferred from the viewpoint of synthesis. Examples thereof include $CF_3-$, $C_2F_5-$, $C_4F_9-$, $C_6F_{13}-$, $C_8F_{17}-$, $C_{10}F_{21}-$, $H(CF_2)_2-$, $H(CF_2)_4-$, $H(CF_2)_6-$, $H(CF_2)_8-$, etc.

Examples of the divalent hydrocarbon groups indicated by X and Y and having 1-6 carbon atoms include alkylene groups such as methylene, ethylene, trimethylene, propylene, butylene, pentamethylene and hexamethylene groups.

Besides, examples of the divalent hydrocarbon group indicated by $R^3$ and having 2-6 carbon atoms include alkylene groups such as ethylene, trimethylene, propylene, butylene, pentamethylene and hexamethylene groups.

Further, the polymerization degree of the fluorine-modified silicone derivative according to the present invention is preferably 2-400, in particular, 2-300.

The fluorine-modified silicone derivative according to the present invention may be basically a silicone the organopolysiloxane chain of which is partly substituted by the siloxane chain of the general formula (1), (2) or (3). Accordingly, there are three aspects of a compound having units of the formula (1) and the formula (4), a compound having units of the formula (2) and the formula (4), and a compound having units of the formula (3) and the formula (4). The terminal group of the compounds according to the present invention may be any one of $R^1$, $R^4$, $R^5$,

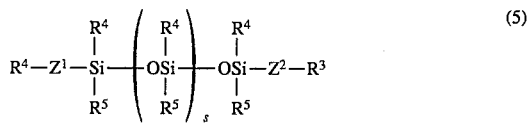

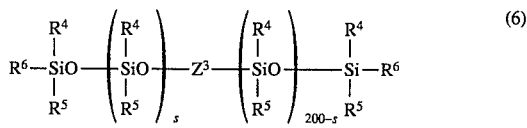

and $+CH_2\frac{1}{t}+OR^3\frac{1}{r}O+CH_2\frac{1}{n}Rf.$

Among the fluorine-modified silicone derivatives according to the present invention, those represented by the following general formulae (5) and (6) are particularly preferred.

(5)

(6)

wherein at least one of $Z^1$ and $Z^2$ means a group selected from the general formulae (1), (2) and (3), the remainder thereof denotes a single bond, $Z^3$ stands for a group selected from the general formulae (1), (2) and (3), $R^6$ is a straight-chain or branched aliphatic hydrocarbon group having 1-20 carbon atoms or an alicyclic or aromatic hydrocarbon group having 5-10 carbon atoms, and s, $R^4$ and $R^5$ have the same meaning as defined above.

The fluorine-modified silicone derivatives according to the present invention are prepared, for example, by reacting a compound having polysiloxane units represented by the following general formulae (7) and (4):

$$\left(\begin{array}{c} R^1 \\ | \\ -SiO- \\ | \\ H \end{array}\right)_p$$

(7)

$$\left(\begin{array}{c} R^4 \\ | \\ -SiO- \\ | \\ R^5 \end{array}\right)_s$$

(4)

with a compound selected from compounds of the general formulae (8), (9) and (11):

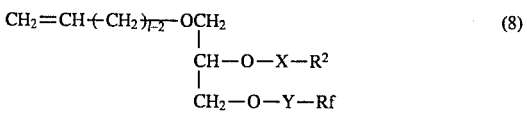

(8)

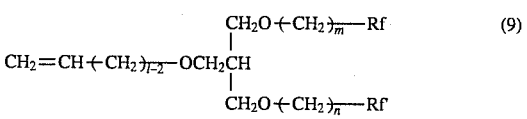

(9)

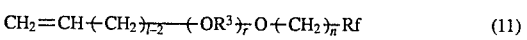

(11)

wherein Rf, Rf', $R^2$, $R^3$, l, m, n and r have the same meaning as defined above.

No particular limitation is imposed on the molecular structure and the like of the silicone derivative used in the preparation process of the present invention so far as it has at least one polysiloxane unit (7). Therefore, various kinds of known compounds may be used. Specific examples of such a silicone derivative include methylpolysiloxanes with one end terminated by hydrogen, such as pentamethyldisiloxane and tridecamethylhexasiloxane, methylpolysiloxanes with both ends terminated with hydrogen, such as tetramethyldisiloxane, hexamethyltrisiloxane, octamethyltetrasiloxane and dodecamethylhexasiloxane, and commercially-available methylhydrogenpolysiloxanes, for example, "TSF484", "TSF483" and the like produced by Toshiba, Silicone Co., Ltd. and "KF99" and the like produced by Shin-Etsu Chemical Co., Ltd.

The perfluoroalkyl compound used in the preparation process of the present invention and represented by the general formula (8) is a novel compound, and can be prepared in accordance with, for example, the following reaction path:

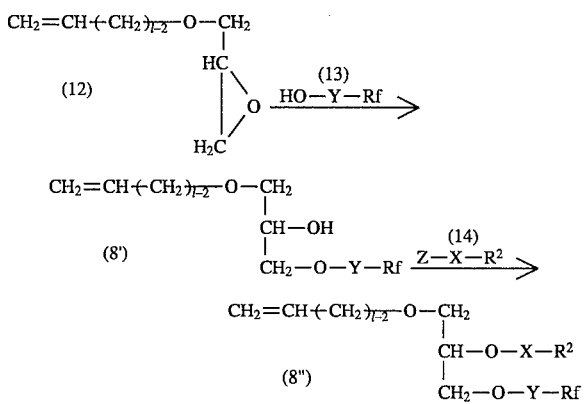

wherein Rf, $R^2$, X, Y and l have the same meaning as defined above, and Z means a halogen atom.

More specifically, a glycidyl ether compound (12) and a fluorine-containing alcohol (13) can be reacted under basic conditions, thereby obtaining a perfluoroalkyl compound (8') in which X is a single bond and $R^2$ is a hydrogen atom. This compound can be then reacted with a compound (14), thereby obtaining a perfluoroalkyl compound (8"). In this reaction, the fluorine-containing alcohol (13) is used in an amount of at least 1 mol equivalent, preferably 1.5–2.5 mol equivalents based on the glycidyl ether compound (12). Besides, the compound (14) is used in an amount of at least 1 mol equivalent, preferably 1.1–1.5 mol equivalents based on the perfluoroalkyl compound (8'). Examples of the base include alkali metals, alkali metal hydrides, alkali metal hydroxides, alkaline earth metal hydrides, alkaline earth metal hydroxides, quaternary ammonium salts, pyridine and the like. The reaction is conducted by using a solvent as needed and heating with stirring in a temperature range of from 30° C. to 150° C., preferably from 40° C. to 100° C.

The compound represented by the general formula (9) is also a novel compound, and can be prepared in accordance with, for example, the following reaction scheme:

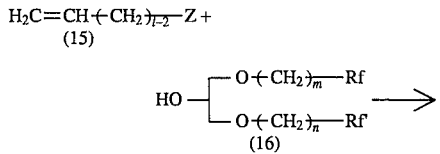

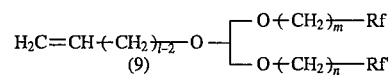

wherein Z means a halogen atom, and l, m, n, Rf and Rf' have the same meaning as defined above.

More specifically, a halogenated alkene (15) and a fluorine-containing alcohol (16) can be reacted under basic conditions, thereby obtaining the compound (9). In this reaction, the compound represented by the general formula (15) is used in an amount of at least 1 mol equivalent, preferably at least 1.5 mol equivalents based on the compound represented by the general formula (16). Examples of the base include alkali metals, alkali metal hydrides, alkali metal hydroxides, alkaline earth metal hydrides, alkaline earth metal hydroxides, quaternary ammonium salts, pyridine and the like. The reaction is conducted by using a solvent as needed and heating with stirring in a temperature range of from 30° C. to 150° C., preferably from 40° C. to 100° C.

In the above reaction scheme, the compound represented by the general formula (16) can be obtained easily and cheaply by reacting a compound of the following general formula (17):

$$Rf(CH_2)_mOH \qquad (17)$$

wherein Rf and m have the same meaning as defined above, with epichlorohydrin in the presence of an alkali metal hydroxide (Japanese Patent Application Laid-Open No. 193236/1989).

The compound represented by the general formula (11) can be prepared in accordance with, for example, the following reaction path:

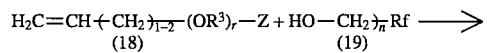

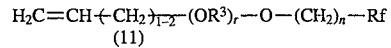

wherein Z means a halogen atom, and Rf, $R^3$, l, n and r have the same meaning as defined above.

More specifically, a halogenated alkene (18) and a fluorine-containing alcohol (19) can be reacted under basic conditions, thereby obtaining the compound (11). In this reaction, the compound represented by the general formula (18) is used in an amount of at least 1 mol equivalent, preferably at least 1.5 mol equivalents based on the compound represented by the general formula (19). Examples of the base include alkali metals, alkali metal hydrides, alkali metal hydroxides, alkaline earth metal hydrides, alkaline earth metal hydroxides, quaternary ammonium salts, pyridine and the like. The reaction is conducted by using a solvent as needed and heating with stirring in a temperature range of from 30° C. to 150° C., preferably from 40° C. to 100° C.

The reaction of the thus-obtained compound (8), (9) or (11) with the silicone derivative having polysiloxane units represented by the general formulae (7) and (4) is conducted in the presence of a catalyst. Examples of the catalyst used include catalysts generally used in hydrosilylation, for example, free-radical initiators; photoinitiators; complex compounds of metals such as ruthenium, rhodium, palladium, osmium, iridium and platinum; and those obtained by supporting these catalysts on silica gel or alumina. Of these, chloroplatinic acid, Speier reagent (a solution of chloroplatinic acid in isopropyl alcohol) and the like are particularly preferred. No particular limitation is imposed on the amount of the catalyst to be used so far as it is a sufficient amount to facilitate the reaction of the silicone derivative with the compound (8), (9) or (11). However, the amount is preferably within a range of $10^{-6}$–$10^{-1}$ mol per mol of the compound (8), (9) or (11).

In this reaction, it is not essential to use a reaction solvent. However, the reaction may be conducted in a suitable solvent as needed. No particular limitation is imposed on the reaction solvent so far as it does not inhibit the reaction. However, for example, hydrocarbon solvents such as pentane, hexane and cyclohexane; benzolic solvents such as benzene, toluene and xylene; etheric solvents such as diethyl ether and diisopropyl ether; alcoholic solvents such as methanol, ethanol, isopropyl alcohol and butanol are particularly preferred.

The hydrosilylation is allowed to proceed at 0°–200° C. It is however preferable to conduct the reaction at 50°–150° C. in view of reaction rate and coloring of the reaction product. The reaction time is preferably within a range of from about 0.5 to about 24 hours.

Incidentally, in order to control various properties, such as viscosity, solubility and emulsion stability, of the fluorine-modified silicone derivative (A) obtained by the above reaction, it is only necessary to suitably change the combination of the kinds, amounts and the like of the silicone derivative having the polysiloxane units represented by the general formula (7) and (4) and the compound (8), (9) or (11).

The thus-obtained fluorine-modified silicone derivative (A) according to the present invention is excellent in water and oil repellency, and its properties such as viscosity may be controlled as necessary for the end application intended. Therefore, when it is used as an oily substance in a cosmetic composition, the cosmetic composition can be provided with excellent lastingness of makeup and feeling upon use imparted thereto. In this case, no particular limitation is imposed on the amount of the fluorine-modified silicone derivative (A) to be incorporated. However, it is preferable to incorporate it within a range of generally 0.001–90 wt. % (hereinafter indicated merely by "%"), preferably 0.1–70%.

In the cosmetic compositions according to the present invention, which contain the fluorine-modified silicone derivative (A), it is possible to additionally use oily substances employed routinely in cosmetic compositions. Examples of such oily substances include cyclic silicones such as octamethylcyclotetrasiloxane, decamethylcyclopentasiloxane and dodecamethylcyclohexasiloxane; nonvolatile silicones such as methylpolysiloxane, dimethylpolysiloxane and methylphenylpolysiloxane; animal and vegetable oils and fats such as squalane and palm oil; and others including hydrocarbons, higher fatty acid esters, liquid paraffin and liquid isoparaffin.

Further, in the cosmetic compositions according to the present invention, may be used insoluble powders routinely used in cosmetic compositions and insoluble powders treated with silicone or a fluorine compound. No particular limitation is imposed on the insoluble powders so far as they are substantially insoluble in water and oil like pigments and ultraviolet absorbents. Examples thereof include inorganic pigments such as titanium oxide, iron oxides, ultramarine blue, zinc white, magnesium oxide, zirconium oxide, mica, sericite, talc, silica, kaolin, chromium hydroxide and carbon black; organic powders such as nylon powder and powders of polymethyl methacrylate, styrene-divinylbenzene copolymers and polyethylene; organic coloring matter; finely particulate titanium oxide, zinc oxide and flaky zinc oxide as ultraviolet absorbents; and the like. In particular, it is preferable to use a fluorine compound-treated insoluble powder because makeup is prevented from getting out of shape due to the excretion of sebum.

Furthermore, in the cosmetic compositions according to the present invention, ingredients, which are mixed routinely in cosmetic compositions, for example, solid and semisolid oils such as vaseline, lanolin, ceresin, microcrystalline wax, carnauba wax, candelilla wax, higher fatty acids and higher alcohols; water-soluble and oil-soluble polymers; coloring materials such as organic dyes; surfactants such as anionic surfactants, cationic surfactants, nonionic surfactants, dimethylpolysiloxanepolyoxyalkylene copolymers and polyether-modified silicones; and others including water, antiseptics, antioxidants, coloring matter, thickeners, pH regulators, perfume bases, ultraviolet absorbents, moisturizers, blood circulation-facilitating agents, cold sensation-imparting agents, antiperspirants, disinfectants and skin activators may be incorporated suitably, as needed, so far as they do not impede the effects of the inventive silicone derivative.

In the cosmetic compositions according to the present invention, no particular limitation is also imposed on their forms and kinds. They can be formulated in accordance with the methods known per se in the art and are applied to, for example, oily cosmetics, emulsified cosmetics, water-based cosmetics, lip sticks, cheek rouges, foundations, skin cleaners, hair shampoos, hair tonics, hair styling preparations, hair grooming preparations, hair growth stimulants, etc.

EXAMPLES

The present invention will hereinafter be described specifically by the following examples. However, the present invention is not limited to these examples.

Incidentally, in the following examples, part of chemical formulae will be abbreviated as follows:

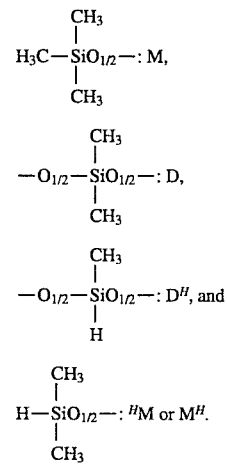

Example 1

Synthesis of

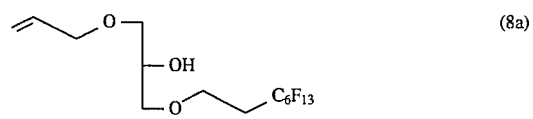

(8a)

A 300-ml three-necked flask equipped with a condenser tube and a mechanical stirrer was charged with 191.4 g (525.8 mmol) of $C_6F_{13}$—$CH_2CH_2$—OH and 1.1 g (26.2 mmol) of NaOH in a nitrogen atmosphere. After the contents were heated to 60° C., 30.0 g (262.9 mmol) of allyl glycidyl ether was added dropwise. After the dropping, the resulting mixture was stirred for 20 hours at 60° C. The reaction mixture was cooled to room temperature and neutralized with 2N HCl, thereby taking out an organic layer. An aqueous layer was extracted twice with $CHCl_3$, and the extract was united with the organic layer. The thus-collected organic layer was dried over anhydrous magnesium sulfate. The desiccant was separated by filtration, and the solvent was distilled off. Unreacted $C_6F_{13}$—$CH_2CH_2$—OH was recovered by distillation under reduced pressure (recovered amount: 93.4 g, recovery: 97%), and 98.6 g of the intended compound (8a) was then obtained as a fraction (colorless, transparent oil, yield: 78%, bp: 82° C./8.5×10$^{-3}$ torr).

Data of $^1$H-NMR (δ ppm, in $CDCl_3$, $CHCl_3$ standard: 7.24 ppm) is shown below.

δ: 2.27–2.70(m,3H,$H_f$,$H_i$), 3.42–3.98(m,9H,$H_c$,$H_d$,$H_e$,$H_g$,$H_h$), 5.13–5.32(m, 2H,$H_a$), 5.79–5.98(m, 1H,$H_b$).

The above $H_a$–$H_i$ indicate respectively protons situated at the following positions:

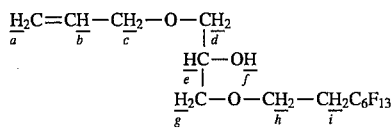

Example 2

Synthesis of

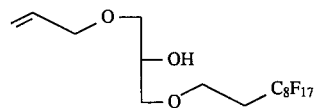 (8b)

A 500-ml three-necked flask equipped with a condenser tube and a mechanical stirrer was charged with 382.3 g (823.8 mmol) of $C_8F_{17}$—$CH_2CH_2$—OH and 1.7 g (41.1 mmol) of NaOH in a nitrogen atmosphere. After the contents were heated to 60° C., 47.0 g (411.9 mmol) of allyl glycidyl ether was added dropwise. After the dropping, the resulting mixture was stirred for 20 hours at 60° C. The reaction mixture was cooled to room temperature and neutralized with 2N HCl, thereby taking out an organic layer. An aqueous layer was extracted twice with $CHCl_3$, and the extract was united with the organic layer. The thus-collected organic layer was dried over anhydrous magnesium sulfate. The desiccant was separated by filtration, and the solvent was distilled off. Unreacted $C_8F_{17}$—$CH_2CH_2$—OH was recovered by distillation under reduced pressure (recovered amount: 169 g, recovery: 88%), and 185.1 g of the intended compound (8b) was then obtained in the form of colorless, transparent oil as a fraction (yield: 78%, bp: 104°–106° C./7.4×10$^{-3}$ torr).

Data of $^1$H-NMR (δ ppm, in $CDCl_3$, $CHCl_3$ standard: 7.24 ppm) is shown below.

δ: 2.25–2.54(m,3H,$H_f$,$H_i$), 3.39–4.02(m,9H,$H_c$,$H_d$,$H_e$,$H_g$,$H_h$), 5.13–5.32(m,2H,$H_a$), 5.78–5.98(m,1H,$H_b$).

The above $H_a$–$H_i$ indicate respectively protons situated at the following positions:

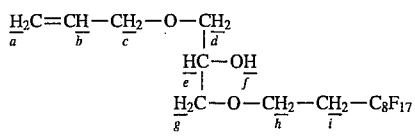

Example 3

Synthesis of

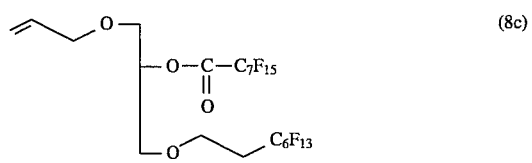 (8c)

A 500-ml four-necked flask equipped with a condenser tube and a mechanical stirrer was charged with 80.0 g (167.4 mmol) of the compound (8a) prepared in Example 1 and 39.7 g (502.1 mmol) of pyridine, to which 79.6 g (184.1 mmol) of $C_7F_{17}$COCl was slowly added dropwise while cooling with ice. After the contents were stirred for 30 minutes while cooling with ice, they were stirred for 2 hours at room temperature. The reaction mixture was added with water and extracted twice with $CHCl_3$, and an organic layer was then dried over anhydrous magnesium sulfate. After the desiccant was separated by filtration, and the solvent was distilled off, 129.8 g of the intended compound (8c) was obtained in the form of colorless, transparent oil as a fraction (yield: 90%, bp: 124°–126° C./1.1×10$^{-2}$ torr).

Data of $^1$H-NMR (δ ppm, in $CDCl_3$, $CHCl_3$ standard: 7.24 ppm) is shown below.

δ: 2.21–2.46(m,2H,$H_h$), 3.61–3.78(m,6H,$H_d$,$H_f$,$H_g$), 3.97(d,J=5.60,2H,$H_c$), 5.14–5.39(m,2H,$H_a$,$H_e$), 5.73–5.92(m, 1H,$H_b$).

The above $H_a$–$H_h$ indicate respectively protons situated at the following positions:

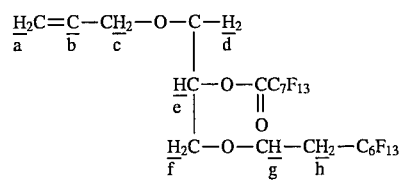

Example 4

Synthesis of

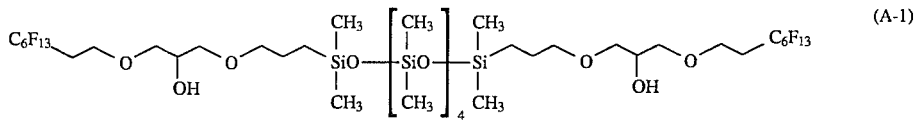

A 100-ml two-necked flask equipped with a condenser tube and a magnetic stirrer was charged with 11.0 g (25.5 mmol) of methylhydrogenpolysiloxane ($^HMD_4M^H$), 29.3 g (61.3 mmol) of the compound (8a) prepared in Example 1 and 101 μl (3.1×10$^{-3}$ mmol) of a 2% solution of chloroplatinic acid in isopropyl alcohol in a nitrogen atmosphere. The contents were stirred for 6 hours at 60° C. The reaction mixture was cooled to room temperature, and unreacted compound (8a) was distilled off under reduced pressure, thereby obtaining 33.6 g of the intended compound (A-1) in the form of colorless, transparent oil (yield: 95%).

Data of $^1$H-NMR (δ ppm, in CDCl$_3$, CHCl$_3$ standard: 7.24 ppm) is shown below.

δ: 0.02–0.06(m, 36H, —SiCH$_3$),
0.45–0.55(m,4H,H$_a$),
1.51–1.66(m,4H,H$_b$),
2.26–2.52(m,6H,H$_h$,H$_i$),
3.36–3.57(m,12H,H$_c$,H$_d$,H$_f$),
3.76(t,J=6.70Hz,4H,H$_g$),
3.88–3.97(m, 2H,H$_e$).

The above H$_a$–H$_i$ indicate respectively protons situated at the following positions:

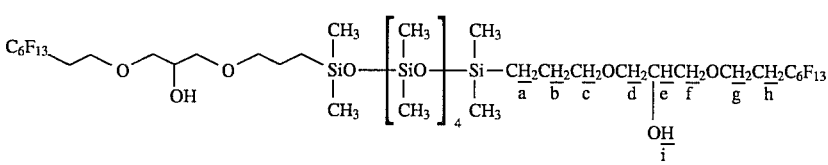

Example 5

Synthesis of

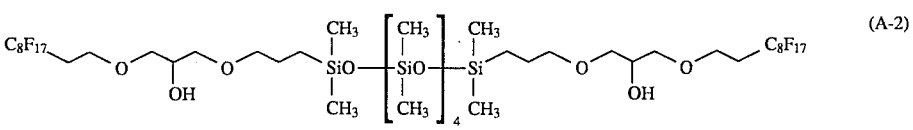

The same equipment as that used in Example 4 was charged with 11.0 g (25.5 mmol) of methylhydrogenpolysiloxane ($^HMD_4M^H$), 35.4 g (61.3 mmol) of the compound (8b) prepared in Example 2 and 40 μl (1.2×10$^{-3}$ mmol) of a 2% solution of chloroplatinic acid in isopropyl alcohol. The contents were treated in the same manner as in Example 4, thereby obtaining 38.0 g of the intended compound (A-2) in the form of colorless, transparent oil (yield: 94%).

Data of $^1$H-NMR (δ ppm, in CDCl$_3$, CHCl$_3$ standard: 7.24 ppm) is shown below.

δ: 0.00–0.05(m, 36H, —SiCH$_3$),
0.46–0.56(m,4H,H$_a$),
1.50–1.66(m,4H,H$_b$),
2.24–2.54(m,6H,H$_h$,H$_i$),
3.35–3.55(m, 12H,H$_c$,H$_d$,H$_f$),
3.76(t,J=6.70Hz,4H,H$_g$),
3.84–3.95(m,2H,H$_e$).

The above H$_a$–H$_i$ indicate respectively protons situated at the following positions:

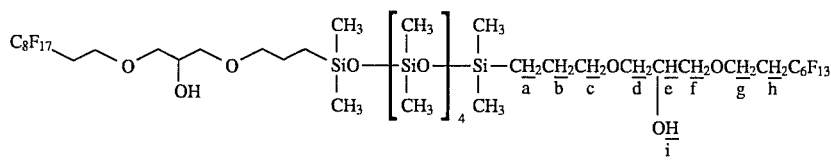

Example 6

Synthesis of

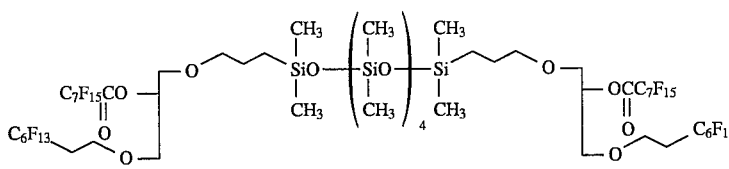
(A-3)

The same equipment as that used in Example 4 was charged with 20 ml of toluene, 6.5 g (15.1 mmol) of methylhydrogenpolysiloxane ($^HMD_4M^H$), 31.7 g (36.2 mmol) of the compound (8c) prepared in Example 3 and 59.8 μl (1.8×10$^{-3}$ mmol) of a 2% solution of chloroplatinic acid in isopropyl alcohol. The contents were treated in the same manner as in Example 4, thereby obtaining 31.2 g of the intended compound (A-3) in the form of colorless, transparent oil (yield: 95%).

Data of $^1$H-NMR (δ ppm, in CDCl$_3$, CHCl$_3$ standard: 7.24 ppm) is shown below.

δ: 0.02–0.05(m, 36H, —SiCH$_3$),
0.44–0.52(m, 4H, H$_a$),
1.47–1.63(m, 4H, H$_b$),
2.21–2.46(m, 4H, H$_h$),
3.34–3.42, 3.58–4.12(m, 16H, H$_c$, H$_d$, H$_f$, H$_g$),
5.28–5.38(m, 2H, H$_e$).

The above H$_a$–H$_h$ indicate respectively protons situated at the following positions:

The same equipment as that used in Example 4 was charged with 20 ml of toluene, 6.4 g (14.9 mmol) of methylhydrogenpolysiloxane (MD$_2$D$_2$M$^H$, product of Toshiba Silicone Co., Ltd.), 31.2 g (35.6 mmol) of the compound (8c) prepared in Example 3 and 58.9 μl (1.8×10$^{-3}$ mmol) of a 2% solution of chloroplatinic acid in isopropyl alcohol. The contents were treated in the same manner as in Example 4, thereby obtaining 25.2 g of the intended compound (A-4) in the form of colorless, transparent oil (yield: 78%).

Data of $^1$H-NMR (δ ppm, in CDCl$_3$, CHCl$_3$ standard: 7.24 ppm) is shown below.

δ: -0.01–0.04(m, 36H, —SiCH$_3$),
0.42–0.51(m, 4H, H$_a$),
1.45–1.61(m, 4H, H$_b$),
2.16–2.45(m, 4H, H$_h$),
3.25–3.40, 3.55–3.80(m, 16H, H$_c$, H$_d$, H$_f$, H$_g$),
5.25–5.39(m, 2H, H$_e$).

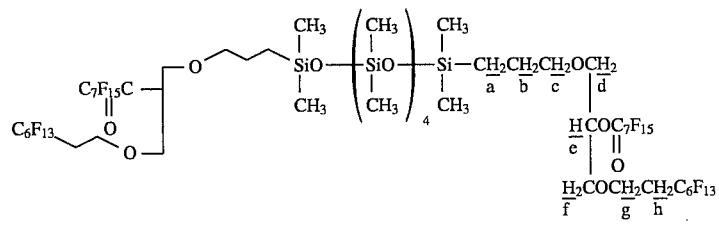

Example 7

Synthesis of

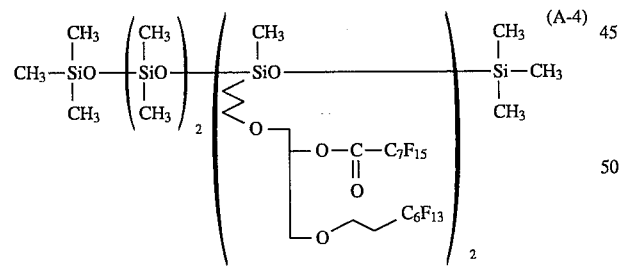
(A-4)

The above H$_a$–H$_h$ indicate respectively protons situated at the following positions:

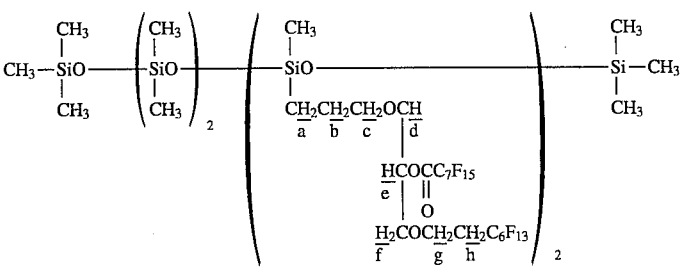

Example 8

Synthesis of

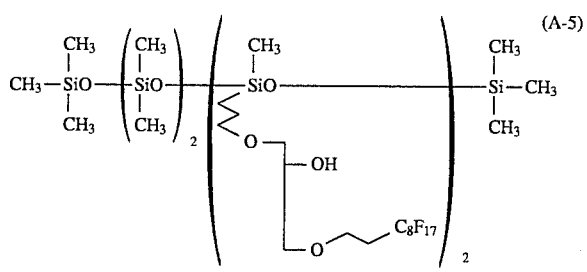

The same equipment as that used in Example 4 was charged with 13.0 g (30.2 mmol) of methylhydrogenpolysiloxane ($MD_2D_2{}^HM$, product of Toshiba Silicone Co., Ltd.), 41.9 g (72.4 mmol) of the compound (8b) prepared in Example 2 and 59.7 μl ($1.8\times10^{-3}$ mmol) of a 2% solution of chloroplatinic acid in isopropyl alcohol. The contents were treated in the same manner as in Example 4, thereby obtaining 38.2 g of the intended compound (A-5) in the form of colorless, transparent oil (yield: 80%).

Data of $^1$H-NMR (δ ppm, in $CDCl_3$, $CHCl_3$ standard: 7.24 ppm) is shown below.

δ: 0.01–0.05(m,36H,—$SiCH_3$),
0.39–0.50(m,4H,$H_a$),
1.48–1.65(m,4H,$H_b$),
2.28–2.50(m,6H,$H_h$,$H_i$),
3.35–3.50(m,12H,$H_c$,$H_d$,$H_f$),
3.74(t,J=6.5Hz,4H,$H_g$),
3.88–3.93(m,2H,$H_e$).

The above $H_a$–$H_i$ indicate respectively protons situated at the following positions:

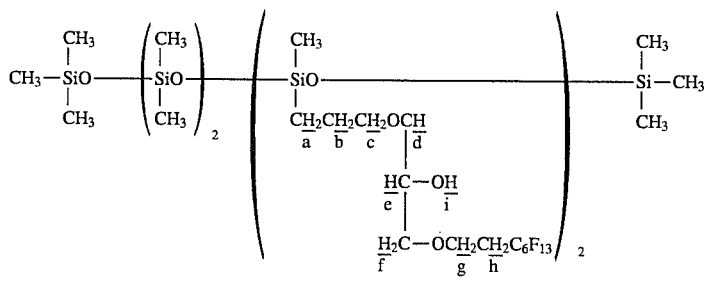

Example 9

Synthesis of

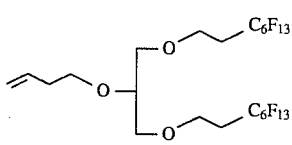

A one-liter three-necked flask equipped with a stirrer and a reflux condenser was charged with a mixed solvent of tetrahydrofuran (250 ml) and dimethylformamide (50 ml), 10.6 g (265.9 mmol) of 60% sodium hydride and 85.8 g (709.2 mmol) of allyl bromide in a nitrogen stream. While stirring the contents at 50° C., a solution of 139.0 g (177.3 mmol) of a compound (16a) [in the formula (16), Rf=Rf'=$C_6F_{13}$, m=n=2] in tetrahydrofuran (180 ml) was added dropwise over 30 minutes. After a reaction was conducted for 5 hours at 50° C., the reaction mixture was allowed to cool. After cold water was added to the reaction mixture to take out an organic layer, an aqueous layer was extracted twice with chloroform, and the extract was united with the organic layer. The thus-collected organic layer was dried over anhydrous magnesium sulfate, and the solvent was distilled off, thereby obtaining a crude product. The thus-obtained crude product was distilled under reduced pressure, thereby obtaining the intended fluorine-containing compound (9a) (115.7 g, 79.0%). Boiling point: 130°–132° C./$1.8\times10^{-2}$ mmHg.

Data of $^1$H-NMR (δ ppm, in $CDCl_3$, $CHCl_3$ standard: 7.24 ppm) is shown below.

δ: 2.20–2.45(m, 4H,$H_g$),
3.49(d,J=3.0Hz, 4H,$H_e$),
3.69(t,J=6.7Hz,4H,$H_f$),
4.05(d,J=5.5Hz,2H,$H_c$),
5.08–5.24(m, 2H,$H_a$),
5.74–5.91(m, 1H,$H_b$).

The above $H_a$–$H_g$ indicate respectively the following protons:

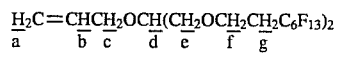

Example 10

Synthesis of fluorine-modified silicone

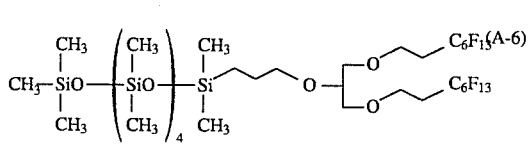

A 100-ml two-necked flask equipped with a condenser tube and a magnetic stirrer was charged with 20 ml of toluene, 10 g (22.5 mmol) of tridecamethylhexasiloxane ($MD_4M^H$), 22.3 g (27.0 mmol) of the compound (9a) prepared in Example 9 and 89.0 μl ($1.6\times10^{-3}$ mmol) of a 2% solution of chloroplatinic acid in isopropyl alcohol in a nitrogen atmosphere. The contents were stirred for 15 hours at 110° C. The reaction mixture was cooled to room temperature and added with 3.0 g of active carbon and 80 ml of hexane. After the resulting mixture was stirred for 1 hour at room temperature, the active carbon was separated by filtration, and the solvent was distilled off. Unreacted compound (9a) was distilled off under reduced pressure, thereby obtaining 22.4 g of the intended compound (A-6) in the form of colorless, transparent oil (yield: 78.4%).

Data of $^1$H-NMR ($\delta$ ppm, in CDCl$_3$, CHCl$_3$ standard: 7.24 ppm) is shown below.

$\delta$: −0.06–0.12(m,39H,—SiC$\underline{H}_3$), 0.41–0.53(m, 2H,H$_a$), 1.46–1.67(m,2H,H$_b$), 2.20–2.58(m,4H,H$_g$), 3.48–3.53(m,7H,H$_c$,H$_d$ and H$_e$), 3.77(t,J=6.6Hz,4H,H$_f$).

The above H$_a$–H$_g$ indicate respectively the following protons:

$$(C_6F_{13}CH_2CH_2OCH_2)_2CHOCH_2CH_2C\underset{a}{H_2}-\underset{}{\overset{CH_3}{\underset{CH_3}{Si}}}O-\left(\overset{CH_3}{\underset{CH_3}{Si}}O\right)_4-\underset{}{\overset{CH_3}{\underset{CH_3}{Si}}}-C\underset{b}{H_2}C\underset{c}{H_2}C\underset{d}{H_2}OC\underset{e}{H}(C\underset{f}{H_2}OC\underset{g}{H_2}CH_2C_6F_{13})_2$$

Example 12

Synthesis of Fluorine-Modified Silicone $$\begin{array}{c}CH_3-SiO-\left(SiO\right)_4-SiO-CH_2CH_2CH_2OCH(CH_2OCH_2CH_2C_6F_{13})_2\\ \text{(with pendant groups)}\end{array}$$

(structure showing C$_6$F$_{13}$ substituents)

Example 11

Synthesis of Fluorine-Modified Silicone $$\begin{array}{c} C_6F_{13}\diagup\diagdown O\diagdown\\ C_6F_{13}\diagup\diagdown O\diagup \end{array}\hspace{-2pt}\begin{array}{c}\\\text{—O—}\end{array}\hspace{-2pt}\begin{array}{c}CH_3\ CH_3\\|\ \ \ |\\ SiO-Si\\|\ \ \ |\\CH_3\ CH_3\end{array}\hspace{-2pt}\begin{array}{c}\text{—O—}\\\\\end{array}\hspace{-2pt}\begin{array}{c} \diagdown O\diagup\diagdown C_6F_{13}\\ \diagup O\diagdown\diagup C_6F_{13}\end{array} \quad (A-8)$$

The same equipment as that used in Example 10 was charged with 20 ml of toluene, 6.5 g (15.1 mmol) of 1,6-dihydriododecamethylhexasiloxane ($^H$MD$_4$M$^H$), 29.9 g (36.3 mmol) of the compound (9a) prepared in Example 9 and 119.6 μl (3.6×10$^{-3}$ mmol) of a 2% solution of chloroplatinic acid in isopropyl alcohol. The contents were treated in the same manner as in Example 10, thereby obtaining 29.9 g of the intended compound (A-7) in the form of colorless, transparent oil (yield: 95.2%).

Data of $^1$H-NMR ($\delta$ ppm, in CDCl$_3$, CHCl$_3$ standard: 7.24 ppm) is shown below.

$\delta$: −0.10–0.10(m,36H,—SiC$\underline{H}_3$), 0.39–0.53(m,4H,H$_a$), 1.42–1.66(m,4H,H$_b$), 2.16–2.60(m,8H,H$_g$), 3.37–3.58(m,14H,H$_c$,H$_d$ and H$_e$), 3.77(t,J=6.6Hz,8H,H$_f$).

The above H$_a$–H$_g$ indicate respectively the following protons:

The same equipment as that used in Example 10 was charged with 2.3 g (17.2 mmol) of 1,1,3,3-tetramethyldisiloxane ($^H$MM$^H$), 33.9 g (41.2 mmol) of the compound (9a) prepared in Example 9 and 81.6 μl (2.5×10$^{-3}$ mmol) of a 2% solution of chloroplatinic acid in isopropyl alcohol. The contents were treated in the same manner as in Example 10, thereby obtaining 27.0 g of the intended compound (A-8) in the form of colorless, transparent oil (yield: 88.2%).

Data of $^1$H-NMR ($\delta$ ppm, in CDCl$_3$, CHCl$_3$ standard: 7.24 ppm) is shown below.

$\delta$: 0.02(s,12H,—SiC$\underline{H}_3$), 0.36–0.53(m,4H,H$_a$), 1.43–1.65(m,4H,H$_b$), 2.21–2.52(m,8H,H$_g$), 3.46–3.59(m,14H,H$_c$,H$_d$ and H$_e$), 3.71(t,8H,H$_f$).

The above H$_a$–H$_g$ indicate respectively the following protons:

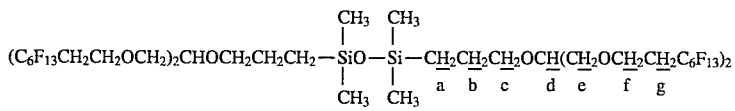

Example 13

Synthesis of Fluorine-Modified Silicone

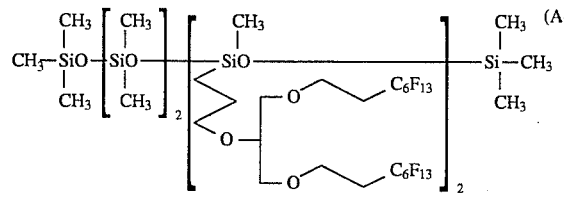

The same equipment as that used in Example 10 was charged with 6.0 g (14.0 mmol) of methylhydrogenpolysiloxane (MD$_2$D$^H_2$M, product of Toshiba Silicone Co., Ltd.) represented by the following formula:

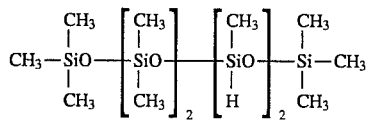

27.6 g (33.5 mmol) of the compound (9a) prepared in Example 9 and 110.5 μl (4.0×10$^{-3}$ mmol) of a 2% solution of chloroplatinic acid in isopropyl alcohol. The contents were treated in the same manner as in Example 10, thereby obtaining 23.2 g of the intended compound (A-9) in the form of colorless, transparent oil (yield: 80.0%).

Data of $^1$H-NMR (δ ppm, in CDCl$_3$, CHCl$_3$ standard: 7.24 ppm) is shown below.

δ: –0.07–0.13(m,36H, —SiCH$_3$),
0.33–0.54(m,4H,H$_a$),
1.42–1.65(m,4H,H$_b$),
2.15–2.49(m,8H,H$_g$),
3.32–3.57(m,14H,H$_c$,H$_d$ and H$_e$),
3.68(t,J=5.9Hz,8H,H$_f$).

The above H$_a$–H$_g$ indicate respectively the following protons:

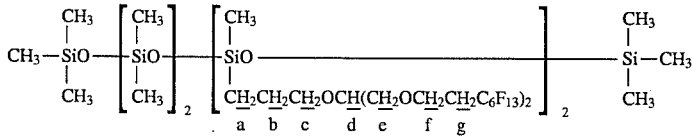

Example 14

Synthesis of Fluorine-Modified Silicone

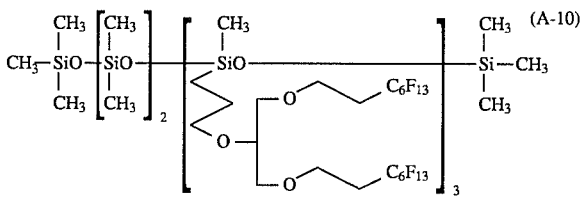

The same equipment as that used in Example 10 was charged with 6.0 g (10.6 mmol) of methylhydrogenpolysiloxane (MD$_3$D$^H_3$M, product of Toshiba Silicone Co., Ltd.) represented by the following formula:

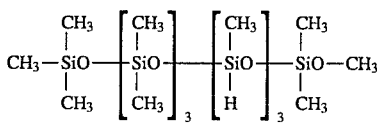

31.6 g (38.3 mmol) of the compound (9a) prepared in Example 9 and 126.0 μl (3.8×10$^{-3}$ mmol) of a 2% solution of chloroplatinic acid in isopropyl alcohol. The contents were treated in the same manner as in Example 10, thereby obtaining 26.1 g of the intended compound (A-10) in the form of colorless, transparent oil (yield: 80.9%).

Data of $^1$H-NMR (δ ppm, in CDCl$_3$, CHCl$_3$ standard: 7.24 ppm) is shown below.

δ: –0.08–0.12(m,45H,—SiCH$_3$),
0.32–0.50(m,6H,H$_a$),
1.41–1.64(m,6H,H$_b$),
2.14–2.49(m,12H,H$_g$),
3.33–3.59(m,21H,H$_c$,H$_d$ and H$_e$),
3.68(t,J=5.9Hz,12H,H$_f$).

The above H$_a$–H$_g$ indicate respectively the following protons:

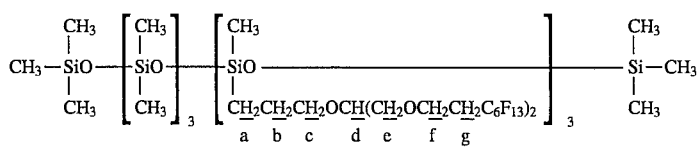

Example 15

Synthesis of

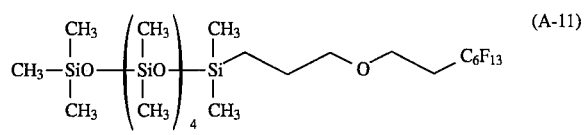

A 100-ml two-necked flask equipped with a condenser tube and a magnetic stirrer was charged with 45 ml of toluene, 15.0 g (33.8 mmol) of tridecamethylhexasiloxane ($MD_4M^H$), 16.4 g (40.5 mmol) of $C_6F_{13}$—$(CH_2)_2$—O—$CH_2CH=CH_2$ (hereinafter abbreviated as "Compound 11a") and 26.7 μl (0.8×10$^{-3}$ mmol) of a 2% solution of chloroplatinic acid in isopropyl alcohol in a nitrogen atmosphere. The contents were stirred for 4 hours at 110° C. The reaction mixture was cooled to room temperature and added with 1.0 g of active carbon. After the resulting mixture was stirred for 1 hour at room temperature, the active carbon was separated by filtration, and the solvent was distilled off. Unreacted Compound (11a) was distilled off under reduced pressure, thereby obtaining 25.8 g of the intended compound (A-11) in the form of colorless, transparent oil (yield: 90%).

Data of $^1$H-NMR (δ ppm, in CDCl$_3$, CHCl$_3$ standard: 7.24 ppm) is shown below.

δ: −0.03–0.02(m,39H,SiC$\underline{H}_3$),
0.41–0.51(m,2H,H$_a$),
1.46–1.61(m, 2H,H$_b$),
2.18–2.47(m, 2H,H$_e$),
3.35(t,J=6–8Hz,2H,H$_c$),
3.61(t,J=6.9Hz,2H,H$_d$).

The above H$_a$–H$_e$ indicate respectively protons situated at the following positions:

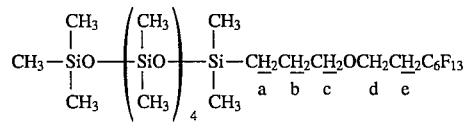

Example 16

Synthesis of

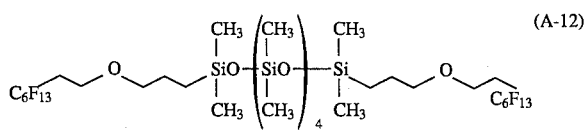

The same equipment as that used in Example 15 was charged with 30 ml of toluene, 11.0 g (25.6 mmol) of methylhydrogenpolysiloxane ($^HMD_4M^H$), 24.8 g (61.4 mmol) of Compound (11a) and 101 μl (3.1×10$^{-3}$ mmol) of a 2% solution of chloroplatinic acid in isopropyl alcohol. The contents were treated in the same manner as in Example 15, thereby obtaining 24.9 g of the intended compound (A-12) in the form of colorless, transparent oil (yield: 79%).

Data of $^1$H-NMR (δ ppm, in CDCl$_3$, CHCl$_3$ standard: 7.24 ppm) is shown below.

δ: 0.01–0.03(m,36H,—SiC$\underline{H}_3$),
0.43–0.51(m,4H,H$_a$),
1.47–1.61(m,4H,H$_b$),
2.20–2.47(m,4H,H$_e$),
3.36(t,J=6.8Hz,4H,H$_c$),
3.64(t,J=6.8Hz, 4H,H$_d$).

The above H$_a$–H$_e$ indicate respectively protons situated at the following positions:

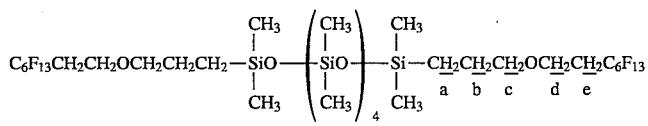

Example 17

Synthesis of

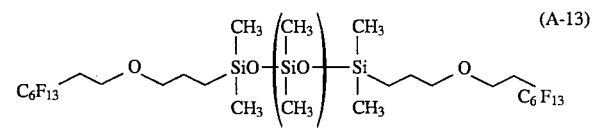

The same equipment as that used in Example 15 was charged with 35 ml of toluene, 11.2 g (19.3 mmol) of methylhydrogenpolysiloxane ($^HMD_6M^H$), 18.8 g (46.5 mmol) of Compound (11a) and 30.7 μl (0.93×10$^{-3}$ mmol) of a 2% solution of chloroplatinic acid in isopropyl alcohol. The contents were treated in the same manner as in Example 15, thereby obtaining 25.4 g of the intended compound (A-13) in the form of colorless, transparent oil (yield: 95%).

Data of $^1$H-NMR (δ ppm, in CDCl$_3$, CHCl$_3$ standard: 7.24 ppm) is shown below.

δ: −0.02–0.02(m,48H,—SiC$\underline{H}_3$),
0.43–0.51(m,4H,H$_a$),
1.48–1.62(m,4H,H$_b$),
2.20–2.47(m,4H,H$_e$),
3.34(t,J=6.9HZ,4H,H$_c$),
3.64(t,J=6.9HZ,4H,H$_d$).

The above $H_a$–$H_e$ indicate, respectively, protons situated at the following positions.

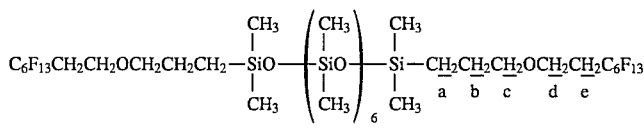

Example 18

Synthesis of

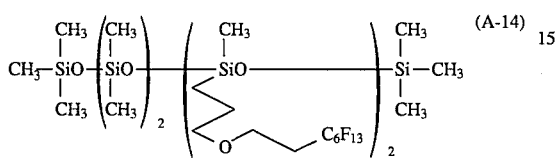

The same equipment as that used in Example 15 was charged with 20 ml of toluene, 8.0 g (18.6 mmol) of methylhydrogenpolysiloxane ($MD_2D_2{}^HM$, product of Toshiba Silicone Co., Ltd.), 18.0 g (44.7 mmol) of Compound (11a) and 29 μl ($0.89 \times 10^{-3}$ mmol) of a 2% solution of chloroplatinic acid in isopropyl alcohol. The contents were treated in the same manner as in Example 15, thereby obtaining 20.3 g of the intended compound (A-14) in the form of colorless, transparent oil (yield: 87%).

Data of $^1$H-NMR (δ ppm, in $CDCl_3$, $CHCl_3$ standard: 7.24 ppm) is shown below.

δ: –0.01–0.03(m,36H,—$SiCH_3$), 0.44–0.52(m,4H,$H_a$), 1.50–1.64(m,4H,$H_b$), 2.20–2.48(m,4H,$H_e$), 3.35(t,J=6.9Hz,4H,$H_c$), 3.69(t,J=6.9Hz,4H,$H_d$).

The above $H_a$–$H_e$ indicate respectively protons situated at the following positions:

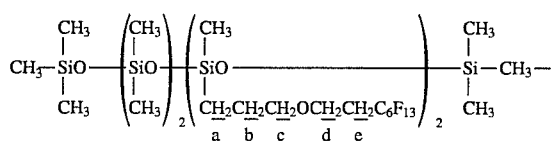

Example 19

Synthesis of

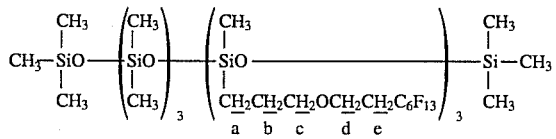

The same equipment as that used in Example 15 was charged with 20 ml of toluene, 7.0 g (12.4 mmol) of methylhydrogenpolysiloxane ($MD_3D_3{}^HM$, product of Toshiba Silicone Co., Ltd.), 18.1 g (44.7 mmol) of Compound (11a) and 29.5 μl ($0.89 \times 10^{-3}$ mmol) of a 2% solution of chloroplatinic acid in isopropyl alcohol. The contents were treated in the same manner as in Example 15, thereby obtaining 19.7 g of the intended compound (A-15) in the form of colorless, transparent oil (yield: 89%).

Data of $^1$H-NMR (δ ppm, in $CDCl_3$, $CHCl_3$ standard: 7.24 ppm) is shown below.

δ: –0.05–0.00(m,45H,—$SiCH_3$), 0.35–0.50(m,6H,$H_a$), 1.44–1.59(m,6H,$H_b$), 2.18–2.42(m,6H,$H_e$), 3.31(t,J=6.9Hz,6H,$H_c$), 3.60(t,J=6.9Hz,6H,$H_d$).

The above $H_a$–$H_e$ indicate respectively protons situated at the following positions:

Example 20

Synthesis of

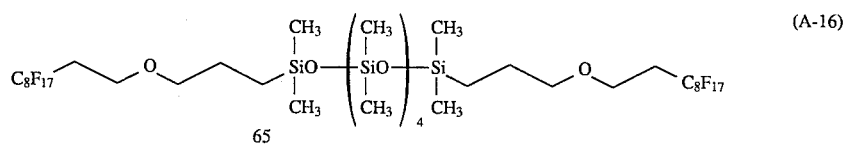

The same equipment as that used in Example 15 was charged with 50 ml of xylene, 15.0 g (34.8 mmol) of methylhydrogenpolysiloxane ($^H MD_4 M^H$), 42.1 g (83.5 mmol) of $C_8F_{17}-(CH_2)_2-O-CH_2CH=CH_2$ (11b) and 137 μl (4.2×10$^{-3}$ mmol) of a 2% solution of chloroplatinic acid in isopropyl alcohol. The contents were treated in the same manner as in Example 15, thereby obtaining 47.0 g of the intended compound (A-16) in the form of colorless, transparent oil (yield: 94%).

Data of $^1$H-NMR (δ ppm, in CDCl$_3$, CHCl$_3$ standard: 7.24 ppm ) is shown below.

δ: 0.02–0.06(m,36H,—SiC$\underline{H}_3$), 0.47–0.56(m, 4H,H$_a$), 1.44–1.67(m, 4H,H$_b$), 2.24–2.50(m,4H,H$_e$), 3.39(t,J=6.86Hz,4H,H$_c$), 3.68(t,J=6.96Hz, 4H,H$_d$).

The above H$_a$–H$_e$ indicate respectively protons situated at the following positions:

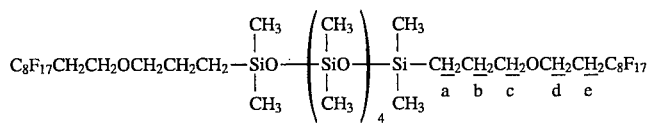

Example 21

Synthesis of

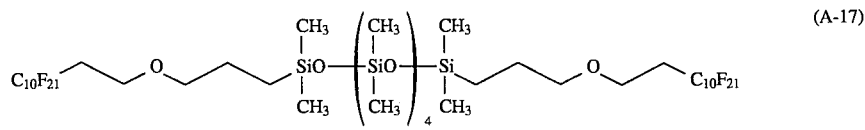
(A-17)

The same equipment as that used in Example 15 was charged with 12 ml of xylene, 12.0 g (27.8 mmol) of methylhydrogenpolysiloxane ($^H MD_4 M^H$), 40.4 g (66.8 mmol) of $C_{10}F_{21}-(CH_2)_2-O-CH_2CH=CH_2$ (11c) and 101 μl (3.1×10$^{-3}$ mmol) of a 2% solution of chloroplatinic acid in isopropyl alcohol. The contents were treated in the same manner as in Example 15, thereby obtaining 41.0 g of the intended compound (A-17) in the form of colorless, transparent wax (yield: 90%). The melting point of this product was 37.0° C.

Data of $^1$H-NMR (δ ppm, in CDCl$_3$, CHCl$_3$ standard: 7.24 ppm) is shown below.

δ: −0.02–0.02(m,36H,—SiC$\underline{H}_3$), 0.43–0.51(m,4H,H$_a$), 1.46–1.62(m,4H,H$_b$), 2.19–2.46(m,4H,H$_e$), 3.34(t,J=6.88Hz,4H,H$_c$), 3.64(t,J=6.96Hz,4H,H$_d$).

The above H$_a$–H$_e$ indicate respectively protons situated at the following positions:

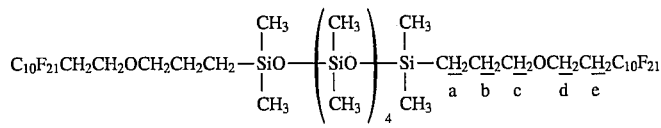

Test Example 1

The fluorine-modified silicones (A-1), (A-2), (A-3) and (A-4) synthesized in Examples 4, 5, 6 and 7, respectively, were compared with conventional products (Comparative Examples 1–3) in physical properties. Evaluated properties and results are shown in Table 1.

TABLE 1

| | Water*$^4$ resistance | Oil*$^5$ resistance | Solubility*$^6$ |
|---|---|---|---|
| A-1 | ⊙ | ○ | ○ |
| A-2 | ⊙ | ⊙ | ○ |
| A-3 | ⊙ | ⊙ | ○ |
| A-4 | ○ | ⊙ | ○ |
| Comp. Ex. 1*$^1$ | ⊙ | x | ○ |
| Comp. Ex. 2*$^2$ | ⊙ | ⊙ | x |
| Comp. Ex. 3*$^3$ | ⊙ | x | ○ |

*$^1$Trifluoropropylsilicone ("X-22-820", product of Shin-Etsu Chemical Co., Ltd.)

TABLE 1-continued

*$^2$"FSL-300" (product of Asahi Glass Co. Ltd.). This product has the following chemical formula:

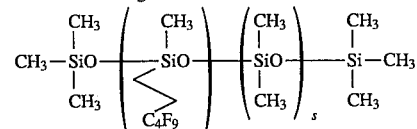

*$^3$Polydimethylsiloxane ("KF-96", product of Shin-Etsu Chemical Co., Ltd.).
*$^4$Water resistance was ranked as ⊙ where a contact angle with water (an angle formed by the oil film of each oily substance and a water droplet) was 80° or wider, or o where the contact angle was not narrower than 60°, but narrower than 80°.
*$^5$Oil resistance was ranked as ⊙ where a contact angle with squalane (an angle formed by a mixture of each oily substance and fluorine-treated powder, and a squalane droplet) was 50° or wider, o where the contact angle was not narrower than 40°, but narrower than 50°, or x where the contact angle was narrower than 40°.
*$^6$Solubility of each test sample in octamethylcyclotetrasiloxane

TABLE 1-continued was determined and ranked as o where it was soluble, or x where it was separate.

Apparent from Table 1, it is understood that the fluorine-modified silicone derivatives according to the present invention are better in water and oil repellency and also good in compatibility with the base substance for cosmetic compositions compared with the conventional products.

Test Example 2

The fluorine-modified silicones (A-6) and (A-7) synthesized in Examples 10 and 11, respectively, were compared with the conventional products in physical properties. Evaluated properties and results are shown in Table 2.

TABLE 2

|  | Water*4 resistance | Oil*5 resistance | Solubility*6 | Viscosity*7 |
|---|---|---|---|---|
| A-6 | o | o | o | ⊚ |
| A-7 | ⊚ | ⊚ | o | ⊚ |
| Comp.*1 Ex. 1 | ⊚ | x | o | x |
| Comp.*2 Ex. 2 | ⊚ | ⊚ | x | x |
| Comp.*3 Ex. 3 | ⊚ | x | o | ⊚ |

*1, *2, *3, *4, *5 and *6: Having the same meaning as in Table 1.
*7: Ranked as ⊚ where viscosity was lower than 35 cst, o where viscosity was not lower than 35 cst, but lower than 80 cst, or x where viscosity was not lower than 80 cst.

Test Example 3

The fluorine-modified silicones (A-12), (A-14), (A-15), (A-16) and (A-17) synthesized in Examples 16, 18, 19, 20 and 21, respectively were compared with the conventional products (Comparative Examples 1–3) in physical properties. Evaluated properties and results are shown in the following table.

TABLE 3

|  | Water*4 resistance | Oil*5 resistance | Solubility*6 | Viscosity*7 |
|---|---|---|---|---|
| A-12 | ⊚ | o | o | ⊚ |
| A-14 | ⊚ | o | o | ⊚ |
| A-15 | ⊚ | ⊚ | o | o |
| A-16 | ⊚ | ⊚ | o | o |
| A-17 | ⊚ | ⊚ | o | — |
| Comp.*1 Ex. 1 | ⊚ | x | o | x |
| Comp.*2 Ex. 2 | ⊚ | ⊚ | x | x |
| Comp.*3 Ex. 3 | ⊚ | x | o | ⊚ |

*1, *2, *3, *4, *6 and *7: Having the same meaning as in Table 1.
*5: Oil resistance was ranked as ⊚ where a contact angle with squalane [an angle formed by the oil film of each oily substance and oil (squalane)] was 30° or wider, o where the contact angle was not narrower than 20°, but narrower than 30°, or x where the contact angle was narrower than 20°.

Apparent from the results shown in Tables 1–3, it is understood that the fluorine-modified silicone derivatives according to the present invention are better in water and oil repellency, mostly lower in viscosity and also good in compatibility with the base substance for cosmetic compositions compared with the conventional products.

Preparation Example 1

Preparation of Fluorine Compound-Treated Sericite

A one-liter round bottom flask (or kneader) was charged with 100 g of sericite, to which 500 ml of deionized water was added. Thereafter, 33 g of an about 17.5% aqueous solution of a dioxyethylamine salt of a perfluoroalkylphosphoric ester $[(C_mF_{2m+1}C_2H_4O)_yPO(ONH_2(CH_2CH_2OH)_2)_{3-y}]$ [m=6–18 (average chain length: 9), 1<y<2] was added to the resulting mixture to stir them at 40° C. Then, 40 ml of 1N hydrochloric acid was added to lower the pH of the aqueous solution to 3 or lower, thereby depositing perfluoroalkylphosphoric acid on the surface of the powder. Thereafter, the powder was collected by filtration, washed with water and dried to obtain 105 g of the intended fluorine compound-treated sericite.

Examples 22–24 and Comparative Examples 4–5

Two-layer Liquid Foundation

Two-layer liquid foundations having their corresponding compositions shown in Table 4 were separately prepared in accordance with a preparation process described below, and evaluated in lastingness of makeup and feeling upon use in accordance with the following evaluation method. The results are shown in Table 5.

Preparation Process

After a solution of an oil phase is prepared at room temperature, pigments are dispersed therein by a disperser. To this dispersion, a water phase is added with stirring to emulsify them, thereby obtaining the intended two-phase liquid foundation.

TABLE 4

| Component | Ex. 22 | Ex. 23 | Ex. 24 | Comp. Ex. 4 | (wt. %) Comp. Ex. 5 |
|---|---|---|---|---|---|
| (1) Fluorine compound-treated pigments: (treating the following pigments in the same manner as as in Prepn. Ex. 1) | | | | | |
| Titanium oxide | 6.0 | 6.0 | 6.0 | 6.0 | 6.0 |
| Sericite | 8.0 | 8.0 | 8.0 | 8.0 | 8.0 |
| Iron oxide (red, yellow, black) | 1.2 | 1.2 | 1.2 | 1.2 | 1.2 |
| (2) Octamethylcyclotetrasiloxane | 20.0 | 20.0 | 20.0 | 20.0 | 20.0 |
| (3) Dimethylpolysiloxanepolyoxyalkylene copolymer | 1.0 | 1.0 | 1.0 | 1.0 | 1.0 |
| (4) Fluorine-modified silicone (A-1) in Example 4 | 10.0 | — | — | — | — |
| (5) Fluorine-modified silicone (A-7) in Example 11 | — | 10.0 | — | — | — |
| (6) Fluorine-modified silicone (A-16) in | — | — | 10.0 | — | — |

TABLE 4-continued

| Component | Ex. 22 | Ex. 23 | Ex. 24 | Comp. Ex. 4 | (wt. %) Comp. Ex. 5 |
|---|---|---|---|---|---|
| Example 20 | | | | | |
| (7) Dimethylpolysiloxane ("KF-96A", 6 cs, product of Shin-Etsu Chemical Co., Ltd.) | — | — | — | 10.0 | — |
| (8) Fluorine-modified silicone in Comp. Ex. 1 | — | — | — | — | 10.0 |
| (9) Glycerin | 2.0 | 2.0 | 2.0 | 2.0 | 2.0 |
| (10) Ethanol | 15.0 | 15.0 | 15.0 | 15.0 | 15.0 |
| (11) Water | Bal. | Bal. | Bal. | Bal. | Bal. |
| (12) Octyl methoxy-cinnamate | 2.0 | 2.0 | 2.0 | 2.0 | 2.0 |
| (13) Perfume base | Trace | Trace | Trace | Trace | Trace |

Evaluation Method

Lastingness of makeup and feeling upon use:

Ten expert panelists organoleptically evaluated each foundation sample in lastingness of makeup and feeling upon use to rank them in accordance with the following standard:

○: Eight or more panelists judged "good";

Δ: Four to seven panelists judged "good";

x: Three or fewer panelists judged "good".

TABLE 5

| | Lastingness of makeup | Feeling upon use |
|---|---|---|
| Example 22 | ○ | ○ |
| Example 23 | ○ | ○ |
| Example 24 | ○ | ○ |
| Comp. Ex. 4 | x | ○ |
| Comp. Ex. 5 | Δ | x |

As apparent from Table 5, the liquid foundations according to the present invention were superior in lastingness of makeup and feeling upon use to those containing silicone heretofore in use.

Example 25

Powder Foundation

A powder foundation having the following composition was prepared in accordance with a preparation process described below.

Preparation Process

Pigments are mixed and ground in a mill. The thus-ground pigment mixture is transferred to a high-speed blender, to which an intimate mixture obtained by mixing a binder and the like under heat is added, followed by intimate mixing. The thus-obtained intimate mixture is treated in a mill, sifted to make its particle size even and then left over for several days. Thereafter, the mixture is compression-molded in a container such as a metal pan to obtain the powder foundation.

| (Composition) | (wt. %) |
|---|---|
| (1) Fluorine compound-treated pigments (treating the following pigments in the same manner as in Preparation Example 1) | |
| Titanium oxide | 10.0 |
| Sericite | 30.0 |
| Mica | Balance |
| Kaolin | 5.0 |
| Iron oxide red | 0.8 |
| Iron oxide yellow | 2.5 |
| Iron oxide black | 0.1 |
| (2) Fluorine-modified silicone (A-4) in Example 7 | 8.0 |
| (3) Bees wax | 2.0 |
| (4) Antiseptic | 0.2 |
| (5) Perfume base | Trace amount |

Example 26

Cheek Rouge

A cheek rouge having the following composition was obtained in accordance with the same preparation process as in Example 25.

| (Composition) | (wt. %) |
|---|---|
| (1) Silicone-treated pigments (commercially available products; pigments treated with methylhydrogenpolysiloxane) | |
| Kaolin | Balance |
| Mica | 13.0 |
| Titanium oxide | 12.0 |
| Red Color No. 202 | 2.5 |
| Iron oxide (red, yellow, black) | 5.0 |
| (2) Fluorine-modified silicone (A-2) in Example 5 | 7.0 |
| (3) Dimethylpolysiloxane ("KF-96A", 6 cs, product of Shin-Etsu Chemical Co., Ltd.) | 5.0 |
| (4) Antiseptic | 0.1 |
| (5) Perfume base | Trace amount |

Example 27

Powder Eye Shadow

A powder eye shadow having the following composition was obtained in accordance with a preparation process described below.

Preparation Process

The intended powder eye shadow is obtained in the same manner as in Example 25 except that other pigments than mica titanium are previously mixed and ground, and mica titanium is then mixed thereto.

| (Composition) | (wt. %) |
|---|---|
| (1) Water- and oil-repellent powders (those treated in the same manner as in Preparation Example 1 were mixed later on) | |
| Mica titanium | 4.9 |
| Sericite | Balance |
| Mica | 25.0 |
| Iron oxide (red, yellow, black) | 2.0 |
| Ultramarine blue | 9.0 |
| Iron blue | 12.0 |

| (Composition) | (wt. %) |
|---|---|
| (2) Fluorine-modified silicone (A-3) in Example 6 | 8.0 |
| (3) Squalane | 2.0 |
| (4) Vaseline | 1.5 |
| (5) Sorbitan trioleate | 1.0 |
| (6) Antiseptic | 0.1 |
| (7) Perfume base | Trace amount |

Example 28

Two-Way Type Powder Foundation

A two-way type powder foundation having the following composition was obtained in accordance with the same preparation process as in Example 27.

| (Composition) | (wt. %) |
|---|---|
| (1) Silicone-treated pigments (commercially available products; pigments treated with methylhydrogenpolysiloxane) | |
| Mica | Balance |
| Talc | 4.8 |
| Titanium oxide | 14.0 |
| Mica titanium | 3.5 |
| Iron oxide (red, yellow, black) | 8.2 |
| Zinc oxide | 4.5 |
| Aluminum oxide | 10.0 |
| Barium sulfate | 5.0 |
| (2) Fluorine-modified silicone (A-2) in Example 5 | 6.0 |
| (3) Lanolin | 3.0 |
| (4) Vaseline | 1.0 |
| (5) Isopropyl myristate | 1.0 |
| (6) Antiseptic | 1.5 |
| (7) Perfume base | Trace amount |

Example 29

Two-Layer Sunscreen Milky Lotion

A two-layer sunscreen milky lotion having the following composition was obtained in accordance with the same preparation process as in Example 22.

| (Composition) | (wt. %) |
|---|---|
| (1) Octamethylcyclotetrasiloxane | 25.0 |
| (2) Fluorine-modified silicone (A-1) in Example 4 | 15.0 |
| (3) Dimethylpolysiloxane-polyoxyalkylene copolymer | 1.0 |
| (4) Glycerin | 2.0 |
| (5) Ethanol | 12.0 |
| (6) Purified water | Balance |
| (7) Octyl methoxycinnamate | 2.0 |
| (8) Silicone-treated pigments (commercially available products; pigments treated with methylhydrogenpolysiloxane) | |
| Zinc oxide | 5.5 |
| Titanium oxide | 2.0 |
| Talc | 5.0 |
| (9) Perfume base | Trace amount |

Example 30

Nourishing Cream

A nourishing cream having the following composition was obtained in accordance with a preparation process described below.

Preparation Process

Components (1) to (5) are mixed and heated to 75° C. To this mixture, a mixture obtained by mixing Components (6), (7) and (10) and heating to 70° C. is added with stirring to emulsify them. After the emulsification, the resulting emulsion is cooled to 60° C. and added with Components (8) and (9). The resulting mixture is cooled further to room temperature, thereby obtained the nourishing cream.

| (Composition) | (wt. %) |
|---|---|
| (1) Polyoxyethylene (50) hardened castor oil | 2.0 |
| (2) Potassium sulfate | 0.5 |
| (3) Fluorine-modified silicone (A-4) in Example 7 | 6.0 |
| (4) Liquid paraffin | 5.0 |
| (5) Hexadecyl-2-ethyl hexanoate | 2.0 |
| (6) Sodium benzoate | 0.3 |
| (7) Propylene glycol | 2.0 |
| (8) dl-$\alpha$-Tocopherol acetate | 0.1 |
| (9) Perfume base | 0.1 |
| (10) Purified water | Balance |

Example 31

Hand Cream

A hand cream having the following composition was obtained in accordance with a preparation process described below.

Preparation Process

Components (1) to (5) are mixed and heated to 75° C. To this mixture, a mixture of Components (6) to (8) heated to 75° C. is gradually added with stirring to emulsify them. The resulting emulsion is cooled to room temperature, thereby obtained the hand cream.

| (Composition) | (wt. %) |
|---|---|
| (1) Polyoxyethylene (20) sorbitan palmitate | 1.5 |
| (2) Aluminum chloride | 0.8 |
| (3) Isopropyl myristate | 4.5 |
| (4) Dimethylpolysiloxane ("KF-96A", 6 cs, product of Shin-Etsu Chemical Co., Ltd.) | 4.0 |
| (5) Fluorine-modified silicone (A-3) in Example 6 | 6.0 |
| (6) Methyl para-hydroxybenzoate | 0.2 |
| (7) Sorbitol | 10.0 |
| (8) Purified water | Balance |

Example 32

Creamy Foundation (water-in-oil type)

A creamy foundation having the following composition was obtained in accordance with a preparation process described below.

Preparation Process

Components (1) to (6) are mixed and heated to 75° C. Component (7) is dispersed by a disperser in this mixture. A mixture of Components (9) to (14) heated to 75° C. is gradually added to the dispersion with stirring to emulsify them. Thereafter, the resulting emulsion is cooled to 30° C. and added with Components (8) and (15). The resulting mixture is cooled further to room temperature, thereby obtained the intended creamy foundation (W/O type)

| (Composition) | (wt. %) |
|---|---|
| (1) Dimethylpolysiloxane-polyoxyalkylene copolymer | 1.0 |
| (2) Fluorine-modified silicone (A-4) in Example 7 | 10.0 |
| (3) Dimethylpolysiloxane ("KF-96A", 6 cs, product of Shin-Etsu Chemical Co., Ltd.) | 5.0 |
| (4) Aluminum stearate | 0.2 |
| (5) 1-Isostearoyl-3-myristoyl-glycerol | 2.0 |
| (6) Octyl methoxycinnamate | 2.0 |
| (7) Fluorine compound-treated pigments (treating the following pigments in the same manner as in Preparation Example 1) | |
| Talc | 5.0 |
| Titanium oxide | 9.0 |
| Iron oxide (red, yellow, black) | 1.2 |
| (8) Decamethylcyclopentasiloxane | 15.0 |
| (9) Butyl para-hydroxybenzoate | 0.1 |
| (10) Sodium benzoate | 0.2 |
| (11) Magnesium sulfate | 0.5 |
| (12) Glycerin | 5.5 |
| (13) 1,3-Butylene glycol | 2.5 |
| (14) Purified water | Balance |
| (15) Perfume base | 0.1 |

Example 33

Disinfectant Cream

A disinfectant cream having the following composition was obtained in accordance with a preparation process described below.

Preparation Process

Components (6) to (11) are intimately mixed. This mixture is added to the aqueous components of (1) to (5) under stirring to emulsify them, thereby obtaining the intended disinfectant cream.

| (Composition) | (wt. %) |
|---|---|
| (1) Polyoxyethylene (50) hardened castor oil | 0.5 |
| (2) Polyoxyethylene (20) sorbitan palmitate | 1.0 |
| (3) Glycerin | 6.0 |
| (4) 1,3-Butylene glycol | 6.0 |
| (5) Purified water | Balance |
| (6) Squalane | 5.0 |
| (7) Jojoba oil | 5.0 |
| (8) Octamethylcyclotetrasiloxane | 18.0 |
| (9) Octyl methoxycinnamate | 2.0 |
| (10) Fluorine-modified silicone (A-1) in Example 4 | 30.0 |
| (11) Disinfectant ("Irgasun DP-300") | 0.2 |

Example 34

Powder Foundation

Pigments were mixed and ground in a mill. The thus-ground pigment mixture was transferred to a high-speed blender, to which an intimate mixture obtained by mixing a binder and the like under heat was added, followed by intimate mixing. The thus-obtained intimate mixture was treated in a mill, sifted to make its particle size even and then left over for several days. Thereafter, the mixture was compression-molded in a container such as a metal pan to obtain a powder foundation.

| | (wt. %) |
|---|---|
| (1) Water- and oil-repellent powders (those treated in the same manner as in Preparation Example 2 described below were mixed later on) | |
| Titanium oxide | 10.0 |
| Sericite | 30.0 |
| Mica | Balance |
| Kaolin | 5.0 |
| Iron oxide red | 0.8 |
| Iron oxide yellow | 2.5 |
| Iron oxide black | 0.1 |
| (2) Fluorine-modified silicone (A-7) in Example 11 | 8.0 |
| (3) Bees wax | 2.0 |
| (4) Antiseptic | 0.2 |
| (5) Perfume base | Trace amount |

Preparation Example 2

A 1-liter round bottom flask (or kneader) was charged with 150 g of sericite, to which a solution with 7.5 g of an about 1:1 mixture of $C_8F_{17}CH_2OP(O)(OH)_2$ and $(C_8F_{17}CH_2CH_2O)_2P(O)OH$ dissolved under heat (50° C.) in 1500 g of isopropyl alcohol in advance was added. The contents were mixed for 4 hours at 60° C. Thereafter, isopropyl alcohol was distilled off under reduced pressure at 40°–55° C. The residue was dried to obtain 155 g of the intended powder.

Example 35

Cheek Rouge

The intended cheek rouge was obtained in the same manner as in Example 34.

| | (wt. %) |
|---|---|
| (1) Silicone-treated pigments (commercially available products; pigments treated with methylhydrogenpolysiloxane) | |
| Kaolin | Balance |
| Mica | 13.0 |
| Titanium oxide | 12.0 |
| Red Color No. 202 | 2.5 |
| Iron oxide (red, yellow, black) | 5.0 |
| (2) Fluorine-modified silicone (A-6) in Example 9 | 7.0 |
| (3) Dimethylpolysiloxane ("KF-96A", 6 cs, product of Shin-Etsu Chemical Co., Ltd.) | 5.0 |
| (4) Antiseptic | 0.1 |
| (5) Perfume base | Trace amount |

Example 36

Powder Eye Shadow

The intended powder eye shadow was obtained in the same manner as in Example 34 except that other pigments than mica titanium were previously mixed and ground, and mica titanium was then mixed thereto.

|  | (wt. %) |
|---|---|
| (1) Water- and oil-repellent powders (those treated in the same manner as in Preparation Example 2 were mixed later on) | |
| Mica titanium | 4.9 |
| Sericite | Balance |
| Mica | 25.0 |
| Iron oxide (red, yellow, black) | 2.0 |
| Ultramarine blue | 9.0 |
| Iron blue | 12.0 |
| (2) Fluorine-modified silicone (A-8) in Example 12 | 8.0 |
| (3) Squalane | 2.0 |
| (4) Vaseline | 1.5 |
| (5) Sorbitan trioleate | 1.0 |
| (6) Antiseptic | 0.1 |
| (7) Perfume base | Trace amount |

Example 37

Two-Way Type Powder Foundation

The intended two-way type powder foundation was obtained in the same manner as in Example 36.

|  | (wt. %) |
|---|---|
| (1) Silicone-treated pigments (commercially available products; pigments treated with methyl-hydrogenpolysiloxane) | |
| Mica | Balance |
| Talc | 4.8 |
| Titanium oxide | 14.0 |
| Mica titanium | 3.5 |
| Iron oxide (red, yellow, black) | 8.2 |
| Zinc oxide | 4.5 |
| Aluminum oxide | 10.0 |
| Barium sulfate | 5.0 |
| (2) Fluorine-modified silicone (A-9) in Example 13 | 6.0 |
| (3) Lanolin | 3.0 |
| (4) Vaseline | 1.0 |
| (5) Isopropyl myristate | 1.0 |
| (6) Antiseptic | 1.5 |
| (7) Perfume base | Trace amount |

Example 38

Two-Layer Sunscreen Milky Lotion

The intended sunscreen milky lotion was obtained in the same manner as in Example 22.

|  | (wt. %) |
|---|---|
| (1) Octamethylcyclotetrasiloxane | 25.0 |
| (2) Fluorine-modified silicone (A-10) in Example 14 | 15.0 |
| (3) Dimethylpolysiloxane-polyoxyalkylene copolymer | 1.0 |
| (4) Glycerin | 2.0 |
| (5) Ethanol | 12.0 |
| (6) Purified water | Balance |
| (7) Octyl methoxycinnamate | 2.0 |
| (8) Silicone-treated pigments (commercially available products; pigments treated with methyl-hydrogenpolysiloxane) | |
| Zinc oxide | 5.5 |
| Titanium oxide | 2.0 |
| Talc | 5.0 |
| (9) Perfume base | Trace amount |

Example 39

Disinfectant Cream

Components (6) to (11) were intimately mixed. This mixture was added to the aqueous components of (1) to (5) under stirring to emulsify them, thereby obtaining the intended disinfectant cream.

|  | (wt. %) |
|---|---|
| (1) Polyoxyethylene (50) hardened castor oil | 0.5 |
| (2) Polyoxyethylene (20) sorbitan palmitate | 1.0 |
| (3) Glycerin | 6.0 |
| (4) 1,3-Butylene glycol | 6.0 |
| (5) Purified water | Balance |
| (6) Squalane | 5.0 |
| (7) Jojoba oil | 5.0 |
| (8) Octamethylcyclotetrasiloxane | 18.0 |
| (9) Octyl methoxycinnamate | 2.0 |
| (10) Fluorine-modified silicone (A-6) in Example 10 | 30.0 |
| (11) Disinfectant ("Irgasun DP-300") | 0.2 |

Example 40

Powder Foundation

A powder foundation having the following composition was prepared in accordance with a preparation process described below.

Preparation Process

Pigments are mixed and ground in a mill. The thus-ground pigment mixture is transferred to a high-speed blender, to which an intimate mixture obtained by mixing a binder and the like under heat is added, followed by intimate mixing. The thus-obtained intimate mixture is treated in a mill, sifted to make its particle size even and then left over for several days. Thereafter, the mixture is compression-molded in a container such as a metal pan to obtain the powder foundation.

| (Composition) | (wt. %) |
|---|---|
| (1) Fluorine compound-treated pigments (treating the following pigments in the same manner as in Preparation Example 1) | |
| Titanium oxide | 10.0 |
| Sericite | 30.0 |
| Mica | Balance |
| Kaolin | 5.0 |
| Iron oxide red | 0.8 |
| Iron oxide yellow | 2.5 |
| Iron oxide black | 0.1 |
| (2) Fluorine-modified silicone (A-16) in Example 20 | 8.0 |
| (3) Bees wax | 2.0 |
| (4) Antiseptic | 0.2 |
| (5) Perfume base | Trace amount |

Example 41

Cheek Rouge

A cheek rouge having the following composition was obtained in accordance with the same preparation process as in Example 40.

| (Composition) | (wt. %) |
|---|---|
| (1) Silicone-treated pigments (commercially available products; pigments treated with methyl-hydrogenpolysiloxane) | |
|     Kaolin | Balance |
|     Mica | 13.0 |
|     Titanium oxide | 12.0 |
|     Red Color No. 202 | 2.5 |
|     Iron oxide (red, yellow, black) | 5.0 |
| (2) Fluorine-modified silicone (A-15) in Example 19 | 7.0 |
| (3) Dimethylpolysiloxane ("KF-96A", 6 cs, product of Shin-Etsu Chemical Co., Ltd.) | 5.0 |
| (4) Antiseptic | 0.1 |
| (5) Perfume base | Trace amount |

Example 42

Powder Eye Shadow

A powder eye shadow having the following composition was obtained in accordance with a preparation process described below.

Preparation Process

The intended powder eye shadow is obtained in the same manner as in Example 40 except that other pigments than mica titanium are previously mixed and ground, and mica titanium is then mixed thereto.

| (Composition) | (wt. %) |
|---|---|
| (1) Water- and oil-repellent powders (those treated in the same manner as in Preparation Example 1 were mixed later on) | |
|     Mica titanium | 4.9 |
|     Sericite | Balance |
|     Mica | 25.0 |
|     Iron oxide (red, yellow, black) | 2.0 |
|     Ultramarine blue | 9.0 |
|     Iron blue | 12.0 |
| (2) Fluorine-modified silicone (A-16) in Example 20 | 8.0 |
| (3) Squalane | 2.0 |
| (4) Vaseline | 1.5 |
| (5) Sorbitan trioleate | 1.0 |
| (6) Antiseptic | 0.1 |
| (7) Perfume base | Trace amount |

Example 43

Two-Way Type Powder Foundation

A two-way type powder foundation having the following composition was obtained in accordance with the same preparation process as in Example 42.

| (Composition) | (wt. %) |
|---|---|
| (1) Silicone-treated pigments (commercially available products; pigments treated with methyl-hydrogenpolysiloxane) | |
|     Mica | Balance |
|     Talc | 4.8 |
|     Titanium oxide | 14.0 |
|     Mica titanium | 3.5 |
|     Iron oxide (red, yellow, black) | 8.2 |
|     Zinc oxide | 4.5 |
|     Aluminum oxide | 10.0 |
|     Barium sulfate | 5.0 |
| (2) Fluorine-modified silicone (A-14) in Example 18 | 6.0 |
| (3) Lanolin | 3.0 |
| (4) Vaseline | 1.0 |
| (5) Isopropyl myristate | 1.0 |
| (6) Antiseptic | 1.5 |
| (7) Perfume base | Trace amount |

Example 44

Two-Layer Sunscreen Milky Lotion

A two-layer sunscreen milky lotion having the following composition was obtained in accordance with the same preparation process as in Example 22.

| (Composition) | (wt. %) |
|---|---|
| (1) Octamethylcyclotetrasiloxane | 25.0 |
| (2) Fluorine-modified silicone (A-13) in Example 17 | 15.0 |
| (3) Dimethylpolysiloxane-polyoxyalkylene copolymer | 1.0 |
| (4) Glycerin | 2.0 |
| (5) Ethanol | 12.0 |
| (6) Purified water | Balance |
| (7) Octyl methoxycinnamate | 2.0 |
| (8) Silicone-treated pigments (commercially available products; pigments treated with methyl-hydrogenpolysiloxane) | |
|     Zinc oxide | 5.5 |
|     Titanium oxide | 2.0 |
|     Talc | 5.0 |
| (9) Perfume base | Trace amount |

Example 45

Nourishing Cream

A nourishing cream having the following composition was obtained in accordance with a preparation process described below.

Preparation Process

Components (1) to (5) are mixed and heated to 75° C. To this mixture, a mixture obtained by mixing Components (6), (7) and (10) and heating to 70° C. is added with stirring to emulsify them. After the emulsification, the resulting emulsion is cooled to 60° C. and added with Components (8) and (9). The resulting mixture is cooled further to room temperature, thereby obtained the nourishing cream.

| (Composition) | (wt. %) |
|---|---|
| (1) Polyoxyethylene (50) hardened castor oil | 2.0 |
| (2) Potassium sulfate | 0.5 |
| (3) Fluorine-modified silicone (A-17) in Example 21 | 6.0 |
| (4) Liquid paraffin | 5.0 |
| (5) Hexadecyl-2-ethyl hexanoate | 2.0 |
| (6) Sodium benzoate | 0.3 |
| (7) Propylene glycol | 2.0 |
| (8) dl-α-Tocopherol acetate | 0.1 |
| (9) Perfume base | 0.1 |
| (10) Purified water | Balance |

Example 46

Hand Cream

A hand cream having the following composition was obtained in accordance with a preparation process described below.

Preparation Process

Components (1) to (5) are mixed and heated to 75° C. To this mixture, a mixture of Components (6) to (8) heated to 75° C. is gradually added with stirring to emulsify them. The resulting emulsion is cooled to room temperature, thereby obtained the hand cream.

| (Composition) | (wt. %) |
|---|---|
| (1) Polyoxyethylene (20) sorbitan palmitate | 1.5 |
| (2) Aluminum chloride | 0.8 |
| (3) Isopropyl myristate | 4.5 |
| (4) Dimethylpolysiloxane ("KF-96A", 6 cs, product of Shin-Etsu Chemical Co., Ltd.) | 4.0 |
| (5) Fluorine-modified silicone (A-17) in Example 21 | 6.0 |
| (6) Methyl para-hydroxybenzoate | 0.2 |
| (7) Sorbitol | 10.0 |
| (8) Purified water | Balance |

Example 47

Creamy Foundation (water-in-oil type)

A creamy foundation having the following composition was obtained in accordance with a preparation process described below.

Preparation Process

Components (1) to (6) are mixed and heated to 75° C. Component (7) is dispersed by a disperser in this mixture. A mixture of Components (9) to (14) heated to 75° C. is gradually added to the dispersion with stirring to emulsify them. Thereafter, the resulting emulsion is cooled to 30° C. and added with Components (8) and (15). The resulting mixture is cooled further to room temperature, thereby obtained the intended creamy foundation (W/O type)

| (Composition) | (wt. %) |
|---|---|
| (1) Dimethylpolysiloxane-polyoxyalkylene copolymer | 1.0 |
| (2) Fluorine-modified silicone (A-12) in Example 16 | 10.0 |
| (3) Dimethylpolysiloxane ("KF-96A", 6 cs, product of Shin-Etsu Chemical Co., Ltd.) | 5.0 |
| (4) Aluminum stearate | 0.2 |
| (5) 1-Isostearoyl-3-myristoyl-glycerol | 2.0 |
| (6) Octyl methoxycinnamate | 2.0 |
| (7) Fluorine compound-treated pigments (treating the following pigments in the same manner as in Preparation Example 1) | |
| Talc | 5.0 |
| Titanium oxide | 9.0 |
| Iron oxide (red, yellow, black) | 1.2 |
| (8) Decamethylcyclopentasiloxane | 15.0 |
| (9) Butyl para-hydroxybenzoate | 0.1 |
| (10) Sodium benzoate | 0.2 |
| (11) Magnesium sulfate | 0.5 |
| (12) Glycerin | 5.5 |
| (13) 1,3-Butylene glycol | 2.5 |
| (14) Purified water | Balance |
| (15) Perfume base | 0.1 |

Example 48

Disinfectant Cream

A disinfectant cream having the following composition was obtained in accordance with a preparation process described below.

Preparation Process

Components (6) to (11) are intimately mixed. This mixture is added to the aqueous components of (1) to (5) under stirring to emulsify them, thereby obtaining the intended disinfectant cream.

| (Composition) | (wt. %) |
|---|---|
| (1) Polyoxyethylene (50) hardened castor oil | 0.5 |
| (2) Polyoxyethylene (20) sorbitan palmitate | 1.0 |
| (3) Glycerin | 6.0 |
| (4) 1,3-Butylene glycol | 6.0 |
| (5) Purified water | Balance |
| (6) Squalane | 5.0 |
| (7) Jojoba oil | 5.0 |
| (8) Octamethylcyclotetrasiloxane | 18.0 |
| (9) Octyl methoxycinnamate | 2.0 |
| (10) Fluorine-modified silicone (A-12) in Example 16 | 30.0 |
| (11) Disinfectant ("Irgasun DP-300") | 0.2 |

All the various cosmetic compositions obtained above in Examples 25–48 were good in lastingness of makeup and excellent in feeling upon use.

INDUSTRIAL APPLICABILITY

According to the present invention, the fluorine-modified silicone derivatives (A) having such excellent features that they are (1) high in water and oil repellency, (2) good in compatibility with base substances for cosmetic compositions, (3) high in emulsion stability, (4) low in viscosity and not sticky to the touch, and (5) extremely low in irritation to the skin can be obtained easily and simply.

Besides, the cosmetic compositions comprising the fluorine-modified silicone derivative (A) are good in lastingness of makeup and excellent in feeling upon use.

We claim:

1. A fluorine-modified silicone derivative (B) having polysiloxane units represented by the following general formula (4):

(4)

and at least one polysiloxane unit selected from the group consisting of structural units represented by the following general formulae (1) and (2):

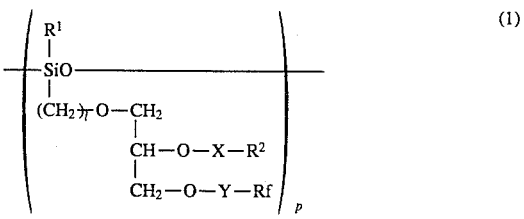

(1)

-continued

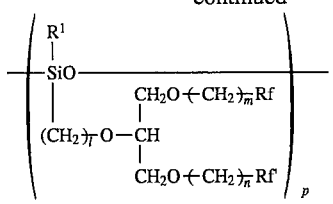 (2)

wherein Rf and Rf' mean individually a perfluoroalkyl group having 6–20 carbon atoms or a ω-H-perfluoroalkyl group represented by the formula $H(CF_2)_t-$ in which t stands for an integer of 6–20, $R^1$, $R^4$ and $R^5$ are identical with or different from each other and mean individually a straight-chain or branched saturated aliphatic hydrocarbon group having 1–20 carbon atoms, or an alicyclic or aromatic hydrocarbon group having 5–10 carbon atoms, $R^2$ denotes a hydrogen atom, a straight-chain or branched aliphatic hydrocarbon group having 1–20 carbon atoms, an alicyclic or aromatic hydrocarbon group having 5–10 carbon atoms, a perfluoroalkyl group having 1–20 carbon atoms, or a ω-H-perfluoroalkyl group represented by the formula $H(CF_2)_u-$ in which u stands for an integer of 1–20, X and Y mean individually a single bond, —CO— or a divalent hydrocarbon group having 1–6 carbon atoms, l stands for a number of 2–16, m and n are individually a number of 1–6, p is a number of 1–200, and s is a number of 0–200.

2. The fluorine-modified silicone derivative (B) according to claim 1, which is represented by the following general formula (5):

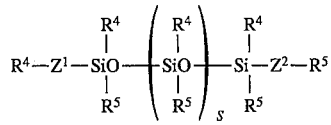 (5)

wherein $Z^1$ is a group selected from the group consisting of general formulae (1) and (2) wherein p is 1, $Z^2$ is a single bond, and s, $R^4$ and $R^5$ have the same meaning as defined in claim 1.

3. The fluorine-modified silicone derivative (B) according to claim 1, which is represented by the following general formula (6):

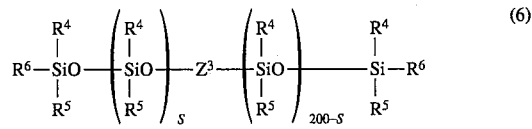 (6)

wherein $Z^3$ means a group selected from the group consisting of units of general formulae (1) and (2), $R^6$ is a straight-chain or branched aliphatic hydrocarbon group having 1–20 carbon atoms or an alicyclic or aromatic hydrocarbon group having 5–10 carbon atoms, and s, $R^4$ and $R^5$ have the same meaning as defined in claim 1.

* * * * *